Figure 4:
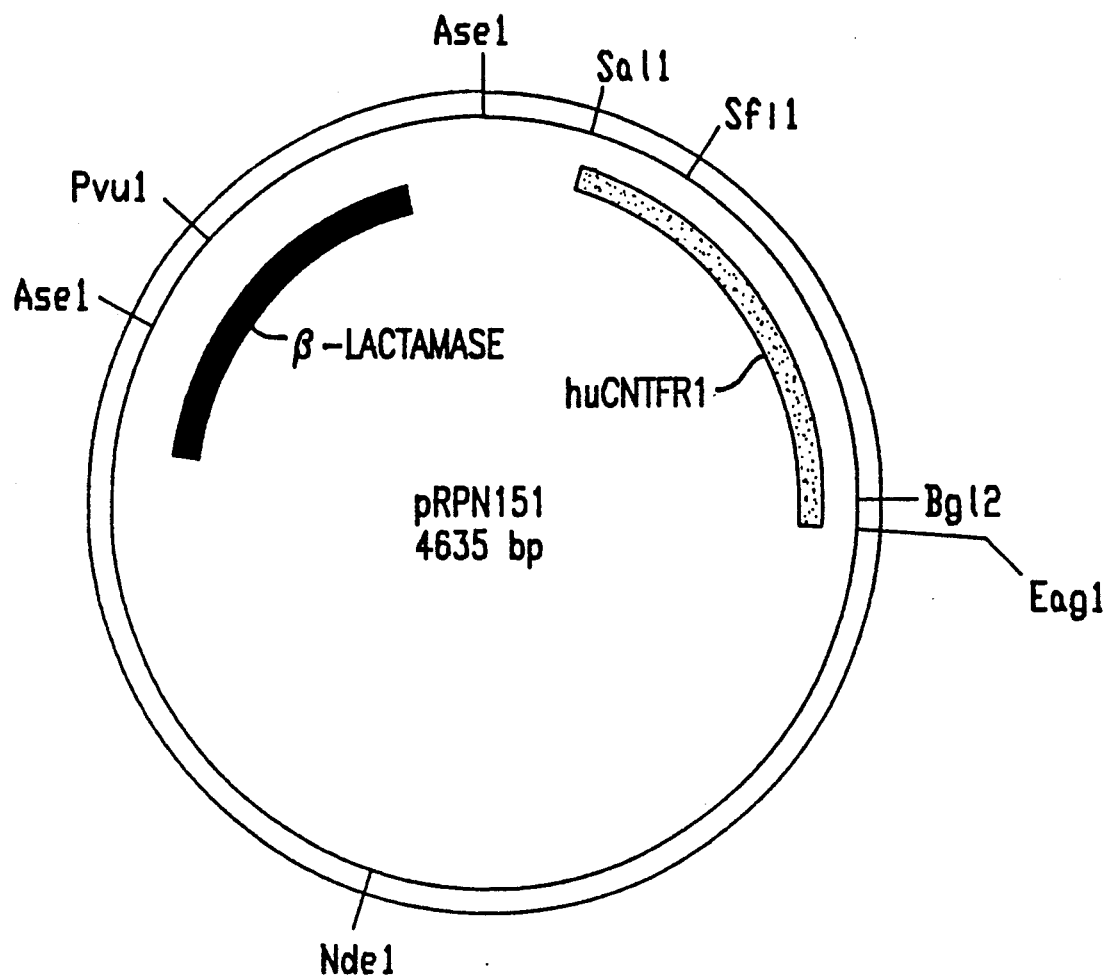

United States Patent [19]

Conover et al.

[11] Patent Number: 5,332,672
[45] Date of Patent: Jul. 26, 1994

[54] PREVENTION OF ES CELL DIFFERENTIATION BY CILIARY NEUROTROPHIC FACTOR

[75] Inventors: Joanne Conover; George D. Yancopoulos, both of Tarrytown

[73] Assignee: Regeneron Pharmaceuticals, Inc., Tarrytown, N.Y.

[21] Appl. No.: 865,878

[22] Filed: Apr. 9, 1992

Related U.S. Application Data

[63] Continuation-in-part of Ser. No. 801,562, Dec. 2, 1991.

[51] Int. Cl.$^5$ .............................................. C12N 5/06
[52] U.S. Cl. .............................. 435/240.2; 435/240.1; 435/69.1; 530/350
[58] Field of Search ...................... 530/350; 435/240.2, 435/69.1, 240.1

[56] References Cited

PUBLICATIONS

Smith et al., 1988, Nature, 336, 688.
Davis et al., 1991, Science, 253, 59.
Rose et al., 1991, Proc. Natl. Acad. Sci., 88, 8641.

*Primary Examiner*—Robert J. Hill, Jr.
*Assistant Examiner*—Sally P. Teng
*Attorney, Agent, or Firm*—Gail M. Kempler

[57] ABSTRACT

The present invention provides for a stable, biologically active CNTF/receptor complex, and hybrids or routants thereof. The invention is also based in part on the discovery that the CNTF/receptor complex promotes differentiation through a signal transduction pathway on target cells that do not express the CNTF receptor. The invention further provides for a specific CNTFR mutant that promotes signal transduction without binding CNTF. The invention also provides for a CNTF/receptor blocking mutant, a mutant possessing a high binding affinity to CNTF, but possessing no signal transducing function. The present invention also identifies receptor components shared by the IL-6, CNTF, LIF and OSM signal transduction pathways, and the initiation of signal transduction based upon the presence of such components. The present invention additionally provides for therapeutic and diagnostic applications dependant on the ability of the CNTF/receptor complex, hybrid or mutant to elicit a physiological response on the appropriate target cell.

1 Claim, 36 Drawing Sheets

GTGCA

CAATCCCCATTAGTAGAGAATGCCAGTGGGTTTAGTCTTTGAGAGTCACATCTCTTATTTG

GACCAGTATAGACAGAAGTAAACCCAGCTGACTTGTTCCTGGGACAGTTGAGTTAAGGG

```
    M   A   F   T   E   H   S   P   L   T   P   H   R   R   D   L   C   S   R   S
ATGGCTTTCACAGAGCATTCACCGCTGACCCCTCACCGTCGGGACCTCTGTAGCCGCTCT

I   W   L   A   R   K   I   R   S   D   L   T   A   L   T   E   S   Y   V   K
ATCTGGCTAGCAAGGAAGATTCGTTCAGACCTGACTGCTCTTACGGAATCCTATGTGAAG

H   Q   G   L   N   K   N   I   N   L   D   S   A   D   G   M   P   V   A   S
CATCAGGGCCTGAACAAGAACATCAACCTGGACTCTGCCGATGGGATGCCAGTGGCAAGC

T   D   Q   W   S   E   L   T   E   A   E   R   L   Q   E   N   L   Q   A   Y
ACTGATCAGTGGAGTGAGCTGACCGAGGCAGAGCGACTCCAAGAGAACCTTCAAGCTTAT

R   F   H   V   L   L   A   R   L   L   E   D   Q   Q   V   H   F   T   P
CGTACCTTCCATGTTTTGTTGGCCAGGCTCTTAGAAGACCAGCAGGTGCATTTTACCCCA
```

FIG. 1A

```
T  E  G  D  F  H  Q  A  I  H  T  L  L  Q  V  A  A  F  A
ACCGAAGGTGACTTCCATCAAGCTATACATACCCTTCTCCAAGTCGCTGCCTTTGCA

Y  Q  I  E  E  L  M  I  L  L  E  Y  K  I  P  R  N  E  A  D
TACCAGATAGAGGAGTTAATGATACTCCTGGAATACAAGATCCCCGCAATGAGGCTGAT

G  M  P  I  N  V  G  D  G  G  L  F  E  K  K  L  W  G  L  K
GGGATGCCTATTAATGTTGGAGATGGTGGTCTCTTTGAGAAGAAGCTGTGGGGCCTAAAG

V  L  Q  E  L  S  Q  W  T  V  R  S  I  H  D  L  R  F  I  S
GTGCTGCAGGAGCTTTCACAGTGGACAGTAAGGTCCATCGACCTTCGTTTCATTTCT

S  H  Q  T  G  I  P  A  R  G  S  H  Y  I  A  N  N  K  K  M
TCTCATCAGACTGGGATCCCAGCACGTGGGAGCCATTATATTGCTAACAACAAGAAAATG

TAGCAGTTAGTCCCTTCTCTCTCCTTACTTTCTCTTCCTTCTAATGGAATATGCGTAGTT
```

FIG. 1B

FIG.2A

```
         10         20         30         40         50         60         70         80
CCTCGAGATC CATTGTGCTC AAAGGGCGGC GGCAGCGGAG GCGGCGGCTC CAGCCGGGCG GGGCGGAGGC TCGGGGGTGG
GGAGCTCTAG GTAACACGAG TTTCCCGCCG CCGTCGCCTC CGCCGCCGAG GCGGCCGCGC GTCGGCCGCG CCGGCTCCG AGCCGCCACC
         90        100        110        120        130        140        150

160        170        180        190        200        210        220        230
GATCCGGCGG GCGGTGCTAG CTCCGGCTC CCTGCCTCGC TGCCTGCCGC GGGCGGTCGG AAGGCGGC
CTAGGCCGCC CGCCACGATC GAGGCGGAG GGACGGACGG AGCGACGGCG GCCCCGAGCC TTCCGGCCG
        240        250        260        270        280        290        300

GCGAAGCCCG GGTGGCCCGA GGGCGCGACT CTAGCCTTGT CACCTCATCT TGCCCCCTTG GTTTGGAAG TCCTGAAGAG
CGCTTCGGGC CCACCGGGCT CCCGGCGCTGA GATCGGAACA GTGGAGTAGA ACGGGGAAC CAAAACCTTC AGGACTTCTC
                                                                         Met Ala Ala Pro Val>

TTGGTCTGGA GGAGGAGGAG GACATTGATC TGCTTGGTGT GTGGCCAGTG GTGAAGAG ATG GCT GCT CCT GTC
AACCAGACCT CCTCCTCCTC CTGTAACTAC ACGAACCACA CACCGGTCAC CACTTCTC TAC CGA CGA GGA CAG
370        380        390        400        410        420        430

310        320        330        340        350        360
CCG TGG GCC TGC TGT GCT GTG CTT GCC GCC GCA GTT GTC GCC CAG AGA CAC AGT CCA
GGC ACC CGG ACG ACA CGA CAC GAA CGG ACA ATG CAG GTC TCT GTG TCA GGT
Pro Trp Ala Cys Cys Ala Val Leu Ala Ala Ala Ala Val Tyr Ala Gln Arg His Ser Pro

CAG GAG GCA CCC CAT GTG CAG TAC GAG CGC CTG GGC TCT GAC GTG ACA CTG CCA TGT GGG ACA
GTC CTC CTC CGT GGG GTA CAC GTC ATG CTC GCG GAC CCG AGA CTG CAC GGT ACA CCC TGT
Gln Glu Ala Pro His Val Gln Tyr Glu Arg Leu Gly Ser Asp Val Thr Leu Pro Cys Gly Thr>

440        450        460        470        480        490
GCA AAC TGG GAT GCT GCG GTG ACG TGG CGG GTA AAT GGG ACA GAC CTG GCC CCT GAC CTG CTC AAC
CGT TTG ACC CTA CGA CGC CAC CGC CAT TTA CCC TGT CTG GAC CGG GGA CTG GAC GAG TTG
Ala Asn Trp Asp Ala Ala Val Thr Trp Arg Val Asn Gly Thr Asp Leu Ala Pro Asp Leu Leu Asn
500        510        520        530        540        550        560

GGC TCT CAG CTG GTG CTC CAT GGC CTG GAA CTG GGC CAC CTG GAC AGT CGT GGC CTC TAC GCC TTC CAC
CCG AGA GTC GAC CAC GAG GTA CCG GAC CTT GAC CCG GTG GAC CCG GTG TCA GCA GTG ATG CGG AAG GTG
Gly Ser Gln Leu Val Leu His Gly Leu Glu Leu Gly His Leu Asp Ser Gly Leu Tyr Ala Cys Phe His>
```

```
                    570           580           590           600           610           620
CGT GAC TCC TGG CAC CTG CGC CAC CAA GTC CAT GTG GGC TTG CCG CGG GCC CTC GGA CAC
GCA CTG AGG ACC GTG GAC GCG GTG GTT CAG GAC GTA CAC CCG AAC GGC GTA CAC CCT GTG
Arg Asp Ser Trp His Leu Arg His Gln Val His Val Gly Leu Pro Arg Glu Pro Val
630                       640           650                         680           690
CTC AGC TGC CGC TCC AAC ACT TAC CCC AAG GGC TTC TAC TGC AGC TGG CAT CTG CCC ACC
GAG TCG ACG GCG AGG TTG TGA ATG GGG TTC CCG AAG ATG ACG TCG ACC GTA GAC GGG TGG
Leu Ser Cys Arg Ser Asn Thr Tyr Pro Lys Gly Phe Tyr Cys Ser Trp His Leu Pro Thr Pro)

700           710           720           730           740           750
ACC TAC ATT CCC AAC ACC TTC AAT GTG CTG ACT GTG CTG CAT GGC TCC AAA ATT ATG GTC TGT GAG AAG
TGG ATG TAA GGG TTG TGG AAG TTA CAC TGA CAC GAC GTA CCG AGG TTT TAA TAC CAG ACA CTC TTC
Thr Tyr Ile Pro Asn Thr Phe Asn Val Leu Thr Val Leu His Gly Ser Lys Ile Met Val Cys Glu Lys
760                       770           780                         800           810
GAC CCG GCC CTC AAG AAC CGC TGC CAC ATT CGC TAC CAC CTG TTC TCC ACC ATC AAG TAC
CTG GGT CGG GAG TTC TTG GCG ACG GTG TAA GCG ATG GTG GAC AAG AGG TGG TAG TTC ATG
Asp Pro Ala Leu Lys Asn Arg Cys His Ile Arg Tyr Met His Leu Phe Ser Thr Ile Lys Try)

820                       830           840           850           860           870           880
AAG GTC TCC ATA AGT GTC AGC AAT GCC CTG GGC CAC AAT GCC ACA GCT ATC ACC TTT GAC GAG TTC
TTC CAG AGG TAT TCA CAG TCG TTA CGG GAC CCG GTA CGG TGT CGA TAG TGG AAA CTG CTC AAG
Lys Val Ser Ile Ser Val Ser Asn Ala Leu Gly His Asn Ala Ile Thr Phe Asp Glu Phe
890                       900           910           920           930           940
ACC ATT GTG AAG CCT GAT CCA GAA AAT GTG GCC CGG CCA GTG CAC CGG CCC AGC AAC CCT CGC
TGG TAA CAC TTC GGA CTA GGT CTT TTA CAC CGG GCC GGT CAC GTG GCC GGG TCG TTG GGA GCG
Thr Ile Val Lys Pro Asp Pro Glu Asn Val Val Ala Arg Pro Val Pro Ser Asn Pro Arg)

950           960           970           980           990           1000          1010
CGG CTG GAG GTG ACG TGG CAG CAG CCC TCG ACC CCT GAG CCT TTT CCT CTC AAG TTC
GCC GAC CTC CAC TGC ACC GTC GTC GGG AGC TGG GGA CTG GGA CTC AGA GAG TTC AAG
Arg Leu Glu Val Thr Trp Gln Thr Pro Ser Thr Pro Asp Pro Glu Ser Phe Pro Leu Lys Phe
```

FIG.2B

FIG. 2C

```
          1020            1030            1040            1050            1060            1070
TTT CTG CGC TAC CGA CCC CTC ATC CTG GAC CAG CAT GTG GAG CTG TCC GAC GGC ACA
AAA GAC GCG ATG GCT GGG GAG TAG GAC CTG GTC ACC GTC GTA CAC CTC GAC AGG CCG TGT
Phe Leu Arg Tyr Arg Pro Leu Ile Leu Asp Gln His Val Glu Leu Ser Asp Gly Thr>
  1080            1090            1100            1110            1120            1130            1140
GCA CAC ACC ATC ACA GAT GCC TAC GCC GGG AAG GAG TAC ATT ATC CAG GTG GCA GCC AAG GAC AAT
CGT GTG TGG TAG TGT CTA CGG ATG CGG CCC TTC CTC ATG TAA TAG GTC CAC CGT CGG TTC CTG TTA
Ala His Thr Ile Thr Asp Ala Tyr Ala Gly Lys Glu Tyr Ile Ile Gln Val Ala Ala Lys Asp Asn
          1150            1160            1170            1180            1190            1200
GAG ATT GGG ACA TGG AGT GAC TGG AGC GTA GCC GCC CAC GCT ACG CCC TGG ACT GAG GAA CCG
CTC TAA CCC TGT ACC TCA CTG ACA CTG TAG TCG CAT CGG GTG CGA TGC GGG ACC TGA CTC CTT GGC
Glu Ile Gly Thr Trp Ser Asp Trp Ser Val Ala Ala His Ala Thr Pro Trp Thr Glu Glu Pro>
  1210            1220            1230            1240            1250            1260            1270
CGA CAC CTC ACC GAG GCC CAG GCT GCG GAG ACC ACG AGC ACC ACC TGG TCC CTG GCA CCC
GCT GTG GAG TGG TGC CTC CGG GTC CGA CGC GCT CTG TGG TGC TCG TGG TGG AGG GAC CGT GGG
Arg His Leu Thr Glu Ala Gln Ala Ala Glu Thr Thr Ser Thr Thr Trp Ser Leu Ala Pro
          1280            1290            1300            1310            1320            1330
CCA CCT ACC ACG AAG ATC TGT GAC CCT GGG GAG CTG GGC AGC CCG GGA CCC TGC GCA CCC
GGT GGA TGG TGC TTC TAG ACA CTG GGA CCC CTC GAC CCG TCG GGC CCT GGG ACG CGT GGG
Pro Pro Thr Thr Lys Ile Cys Asp Pro Gly Glu Leu Gly Ser Pro Gly Pro Cys Ala Pro>
  1340            1350            1360            1370            1380            1390            1400
TTC TTG GTC AGC GTC CCC ATC ACT CTG GCC GCT GCC GCC ACT GCC AGC AGT CTC TTG
AAG AAC CAG TCG CAG GGG TAG TGA GAC CGG CGA CGG CGG CGG TGA CGG TCG TCA GAG AAC
Phe Leu Val Ser Val Pro Ile Thr Leu Ala Ala Ala Ala Thr Ala Ser Ser Leu Leu
          1410            1420            1430            1440            1450            1460            1470
ATC TGAGCC CGGCACCCCA TGAGGACATG CAGAGCACCT GCAGAGGAGC AGGAGGCCGG AGCTGAGCCT
TAG ACTCGG GCCGTGGGGT ACTCCTGTAC GTCTCGTGGA CGTCTCCTCG TCCTCCGGCC TCGACTCGGA
Ile>
```

```
        1480       1490       1500       1510       1520       1530       1540       1550
   GCAGACCCCG GTTTCTATTT TGCACACGGG CAGGAGGACC TTTTGCATTC TCTTCAGACA CAATTGTGTG AGACCCCGGC
   CGTCTGGGGC CAAAGATAAA ACGTGTGCCC GTCCTCCTGG AAAACGTAAG AGAAGTCTGT GTTAAACACC TCTGGGGCCG
        1560       1570       1580       1590
   GGGCCCGGGC CTGCCGCCCC CCAGCCCTGC CGCACCAAGC T
   CCCGGGCCCG GACGGCGGGG GGTCGGGACG GCGTGGTTCG A
```

FIG.2D

Sense:      5' CGCAGTGTCGACAGCaCAGGCGTCACAGTCCACAaGAaGCACCC 3'  EVD-30:43mer
                Sa1I Anti-sense: 3' GCCCCCTGGGACGCGTGGGATTAGCCGGCCGCAGG 5'  EVD-31:35mer
                                             EagI

FIG. 3

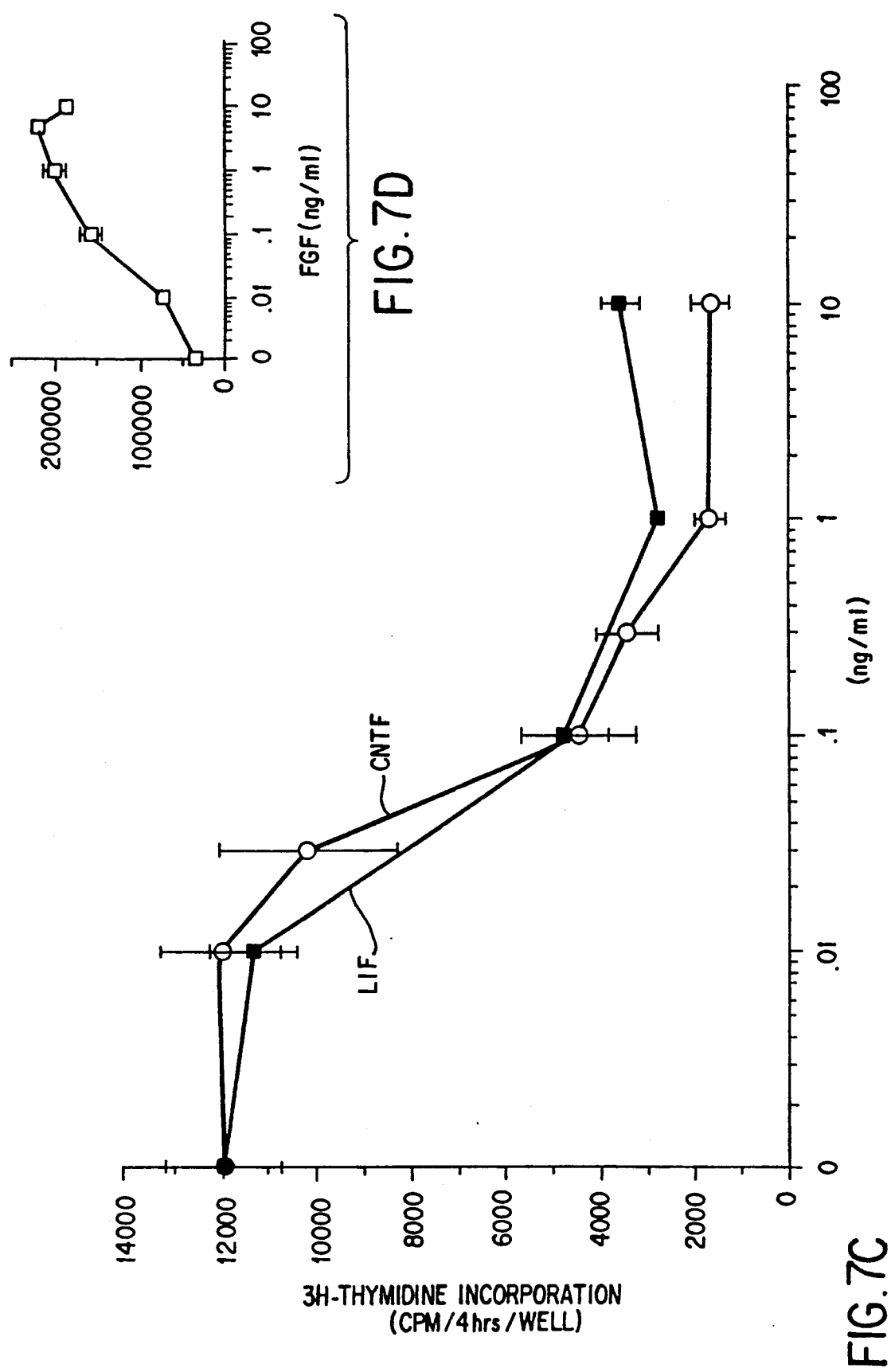

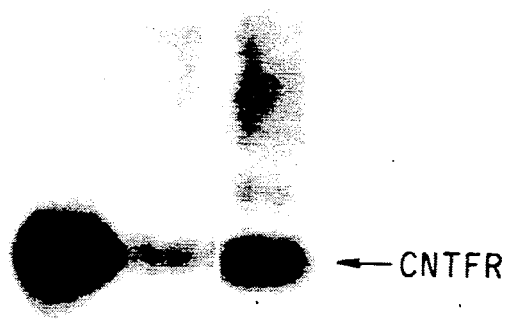
FIG. 8B

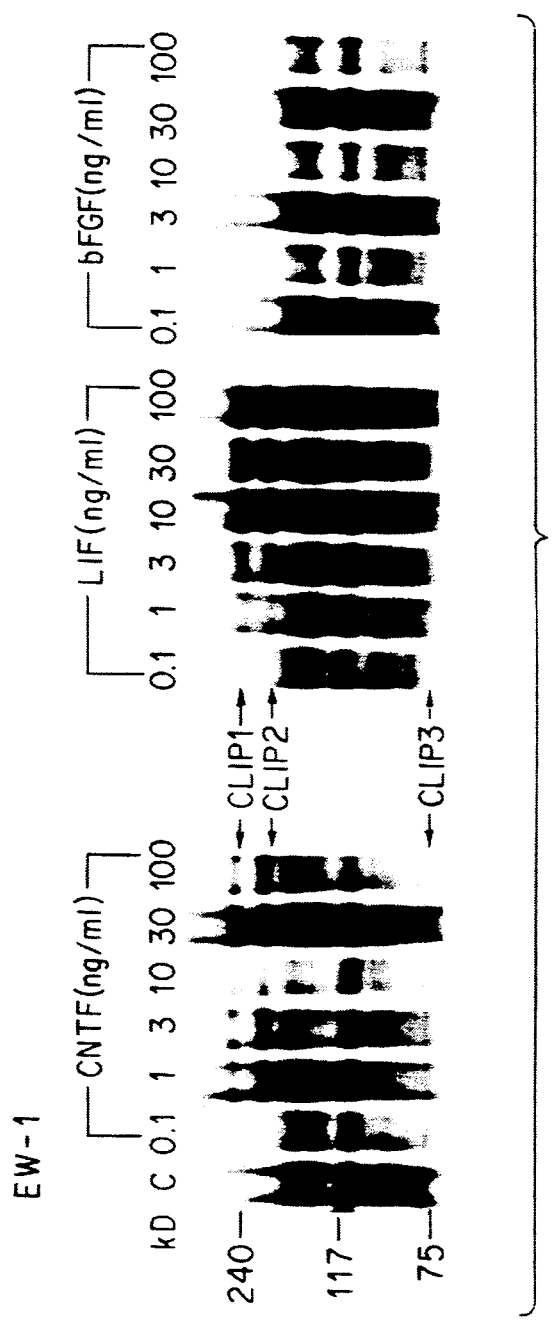

MAH

Control
CNTF
CNTF + H-7
LIF
LIF + H-7 tis11 →

FIG. 13C

MI

Control
mIL-6
mIL-6 + H-7
LIF
LIF + H-7

FIG. 13D

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
( A ) LENGTH: 782 base pairs
( B ) TYPE: nucleic acid
( C ) STRANDEDNESS: single
( D ) TOPOLOGY: unknown ( i i ) MOLECULE TYPE: DNA ( i x ) FEATURE:
( A ) NAME/KEY: CDS
( B ) LOCATION: 126..725

( x i ) SEQUENCE DESCRIPTION: SEQ ID NO:1:

```
GTGCACAATC CCATTAGTAG AGAATGCCAG TGGGTTTAGT CTTTGAGAGT CACATCTCTT      60

ATTTGGACCA GTATAGACAG AAGTAAACCC AGCTGACTTG TTTCCTGGGA CAGTTGAGTT     120
```

| | | | | | | | | | | | | | | | | |
|---|---|---|---|---|---|---|---|---|---|---|---|---|---|---|---|---|
| AAGGG | ATG | GCT | TTC | ACA | GAG | CAT | TCA | CCG | CTG | ACC | CCT | CAC | CGT | CGG | | 167 |
| | Met | Ala | Phe | Thr | Glu | His | Ser | Pro | Leu | Thr | Pro | His | Arg | Arg | | |
| | 1 | | | | 5 | | | | | 10 | | | | | | |
| GAC | CTC | TGT | AGC | CGC | TCT | ATC | TGG | CTA | GCA | AGG | AAG | ATT | CGT | TCA | GAC | 215 |
| Asp | Leu | Cys | Ser | Arg | Ser | Ile | Trp | Leu | Ala | Arg | Lys | Ile | Arg | Ser | Asp | |
| 15 | | | | | 20 | | | | | 25 | | | | | 30 | |
| CTG | ACT | GCT | CTT | ACG | GAA | TCC | TAT | GTG | AAG | CAT | CAG | GGC | CTG | AAC | AAG | 263 |
| Leu | Thr | Ala | Leu | Thr | Glu | Ser | Tyr | Val | Lys | His | Gln | Gly | Leu | Asn | Lys | |
| | | | | 35 | | | | | 40 | | | | | 45 | | |
| AAC | ATC | AAC | CTG | GAC | TCT | GCG | GAT | GGG | ATG | CCA | GTG | GCA | AGC | ACT | GAT | 311 |
| Asn | Ile | Asn | Leu | Asp | Ser | Ala | Asp | Gly | Met | Pro | Val | Ala | Ser | Thr | Asp | |
| | | | 50 | | | | | 55 | | | | | 60 | | | |
| CAG | TGG | AGT | GAG | CTG | ACC | GAG | GCA | GAG | CGA | CTC | CAA | GAG | AAC | CTT | CAA | 359 |
| Gln | Trp | Ser | Glu | Leu | Thr | Glu | Ala | Glu | Arg | Leu | Gln | Glu | Asn | Leu | Gln | |
| | | 65 | | | | | 70 | | | | | 75 | | | | |
| GCT | TAT | CGT | ACC | TTC | CAT | GTT | TTG | TTG | GCC | AGG | CTC | TTA | GAA | GAC | CAG | 407 |
| Ala | Tyr | Arg | Thr | Phe | His | Val | Leu | Leu | Ala | Arg | Leu | Leu | Glu | Asp | Gln | |
| | 80 | | | | | 85 | | | | | 90 | | | | | |
| CAG | GTG | CAT | TTT | ACC | CCA | ACC | GAA | GGT | GAC | TTC | CAT | CAA | GCT | ATA | CAT | 455 |
| Gln | Val | His | Phe | Thr | Pro | Thr | Glu | Gly | Asp | Phe | His | Gln | Ala | Ile | His | |
| 95 | | | | | 100 | | | | | 105 | | | | | 110 | |
| ACC | CTT | CTT | CTC | CAA | GTC | GCT | GCC | TTT | GCA | TAC | CAG | ATA | GAG | GAG | TTA | 503 |
| Thr | Leu | Leu | Leu | Gln | Val | Ala | Ala | Phe | Ala | Tyr | Gln | Ile | Glu | Glu | Leu | |
| | | | | 115 | | | | | 120 | | | | | 125 | | |
| ATG | ATA | CTC | CTG | GAA | TAC | AAG | ATC | CCC | CGC | AAT | GAG | GCT | GAT | GGG | ATG | 551 |
| Met | Ile | Leu | Leu | Glu | Tyr | Lys | Ile | Pro | Arg | Asn | Glu | Ala | Asp | Gly | Met | |
| | | | 130 | | | | | 135 | | | | | 140 | | | |
| CCT | ATT | AAT | GTT | GGA | GAT | GGT | GGT | CTC | TTT | GAG | AAG | AAG | CTG | TGG | GGC | 599 |
| Pro | Ile | Asn | Val | Gly | Asp | Gly | Gly | Leu | Phe | Glu | Lys | Lys | Leu | Trp | Gly | |
| | | 145 | | | | | 150 | | | | | 155 | | | | |
| CTA | AAG | GTG | CTG | CAG | GAG | CTT | TCA | CAG | TGG | ACA | GTA | AGG | TCC | ATC | CAT | 647 |
| Leu | Lys | Val | Leu | Gln | Glu | Leu | Ser | Gln | Trp | Thr | Val | Arg | Ser | Ile | His | |
| | 160 | | | | | 165 | | | | | 170 | | | | | |
| GAC | CTT | CGT | TTC | ATT | TCT | TCT | CAT | CAG | ACT | GGG | ATC | CCA | GCA | CGT | GGG | 695 |
| Asp | Leu | Arg | Phe | Ile | Ser | Ser | His | Gln | Thr | Gly | Ile | Pro | Ala | Arg | Gly | |
| 175 | | | | | 180 | | | | | 185 | | | | | 190 | |
| AGC | CAT | TAT | ATT | GCT | AAC | AAC | AAG | AAA | ATG | TAGCAGTTAG | | TCCCTTCTCT | | | | 745 |
| Ser | His | Tyr | Ile | Ala | Asn | Asn | Lys | Lys | Met | | | | | | | |
| | | | | 195 | | | | | 200 | | | | | | | |
| CTTCCTTACT | TTCTCTTCTA | ATGGAATATG | CGTAGTT | | | | | | | | | | | | | 782 |

( 2 ) INFORMATION FOR SEQ ID NO:2:

( i ) SEQUENCE CHARACTERISTICS:
        ( A ) LENGTH: 200 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:2:

| | | | | | | | | | | | | | | | |
|---|---|---|---|---|---|---|---|---|---|---|---|---|---|---|---|
| Met | Ala | Phe | Thr | Glu | His | Ser | Pro | Leu | Thr | Pro | His | Arg | Arg | Asp | Leu |
| 1 | | | | 5 | | | | | 10 | | | | | 15 | |
| Cys | Ser | Arg | Ser | Ile | Trp | Leu | Ala | Arg | Lys | Ile | Arg | Ser | Asp | Leu | Thr |
| | | | 20 | | | | | 25 | | | | | 30 | | |
| Ala | Leu | Thr | Glu | Ser | Tyr | Val | Lys | His | Gln | Gly | Leu | Asn | Lys | Asn | Ile |
| | | 35 | | | | | 40 | | | | | 45 | | | |
| Asn | Leu | Asp | Ser | Ala | Asp | Gly | Met | Pro | Val | Ala | Ser | Thr | Asp | Gln | Trp |
| | 50 | | | | | 55 | | | | | 60 | | | | |
| Ser | Glu | Leu | Thr | Glu | Ala | Glu | Arg | Leu | Gln | Glu | Asn | Leu | Gln | Ala | Tyr |
| 65 | | | | | 70 | | | | | 75 | | | | | 80 |

-continued

| | | | | | | | | | | | | | |
|---|---|---|---|---|---|---|---|---|---|---|---|---|---|
|Arg|Thr|Phe|His|Val|Leu|Leu|Ala|Arg|Leu|Leu|Glu|Asp|Gln|Gln|Val|
| | | | |85| | | |90| | | |95| | |
|His|Phe|Thr|Pro|Thr|Glu|Gly|Asp|Phe|His|Gln|Ala|Ile|His|Thr|Leu|
| | | |100| | | |105| | | |110| | | |
|Leu|Leu|Gln|Val|Ala|Ala|Phe|Ala|Tyr|Gln|Ile|Glu|Glu|Leu|Met|Ile|
| | |115| | | |120| | | |125| | | | |
|Leu|Leu|Glu|Tyr|Lys|Ile|Pro|Arg|Asn|Glu|Ala|Asp|Gly|Met|Pro|Ile|
|130| | | | |135| | | |140| | | | | |
|Asn|Val|Gly|Asp|Gly|Gly|Leu|Phe|Glu|Lys|Lys|Leu|Trp|Gly|Leu|Lys|
|145| | | |150| | | |155| | | | |160| |
|Val|Leu|Gln|Glu|Leu|Ser|Gln|Trp|Thr|Val|Arg|Ser|Ile|His|Asp|Leu|
| | | |165| | | |170| | | |175| | | |
|Arg|Phe|Ile|Ser|Ser|His|Gln|Thr|Gly|Ile|Pro|Ala|Arg|Gly|Ser|His|
| | |180| | | |185| | | |190| | | | |
|Tyr|Ile|Ala|Asn|Asn|Lys|Lys|Met|
| |195| | | | |200| |

(2) INFORMATION FOR SEQ ID NO:3:

(i) SEQUENCE CHARACTERISTICS:
(A) LENGTH: 1591 base pairs
(B) TYPE: nucleic acid
(C) STRANDEDNESS: double
(D) TOPOLOGY: unknown (ii) MOLECULE TYPE: DNA (cDNA)

(ix) FEATURE:
(A) NAME/KEY: CDS
(B) LOCATION: 289..1404

(xi) SEQUENCE DESCRIPTION: SEQ ID NO:3:

| | | |
|---|---|---|
|CCTCGAGATC CATTGTGCTC AAAGGGCGGC GGCAGCGGAG GCGGCGGCTC CAGCCGGCGC| |60|
|GGCGCGAGGC TCGGCGGTGG GATCCGGCGG GCGGTGCTAG CTCCGCGCTC CCTGCCTCGC| |120|
|TCGCTGCCGG GGGCGGTCGG AAGGCGCGGC GCGAAGCCCG GGTGGCCCGA GGGCGCGACT| |180|
|CTAGCCTTGT CACCTCATCT TGCCCCCTTG GTTTTGGAAG TCCTGAAGAG TTGGTCTGGA| |240|
|GGAGGAGGAG GACATTGATG TGCTTGGTGT GTGGCCAGTG GTGAAGAG ATG GCT GCT| |297|

Met Ala Ala
                                                      1

| | | |
|---|---|---|
|CCT GTC CCG TGG GCC TGC TGT GCT GTG CTT GCC GCC GCC GCC GCA GTT|  |345|
|Pro Val Pro Trp Ala Cys Cys Ala Val Leu Ala Ala Ala Ala Ala Val| | |
|    5               10                  15                      | | |
|GTC TAC GCC CAG AGA CAC AGT CCA CAG GAG GCA CCC CAT GTG CAG TAC|  |393|
|Val Tyr Ala Gln Arg His Ser Pro Gln Glu Ala Pro His Val Gln Tyr| | |
| 20              25                  30              35         | | |
|GAG CGC CTG GGC TCT GAC GTG ACA CTG CCA TGT GGG ACA GCA AAC TGG|  |441|
|Glu Arg Leu Gly Ser Asp Val Thr Leu Pro Cys Gly Thr Ala Asn Trp| | |
|             40                  45                  50         | | |
|GAT GCT GCG GTG ACG TGG CGG GTA AAT GGG ACA GAC CTG GCC CCT GAC|  |489|
|Asp Ala Ala Val Thr Trp Arg Val Asn Gly Thr Asp Leu Ala Pro Asp| | |
|             55                  60                  65         | | |
|CTG CTC AAC GGC TCT CAG CTG GTG CTC CAT GGC CTG GAA CTG GGC CAC|  |537|
|Leu Leu Asn Gly Ser Gln Leu Val Leu His Gly Leu Glu Leu Gly His| | |
|         70                  75                  80             | | |
|AGT GGC CTC TAC GCC TGC TTC CAC CGT GAC TCC TGG CAC CTG CGC CAC|  |585|
|Ser Gly Leu Tyr Ala Cys Phe His Arg Asp Ser Trp His Leu Arg His| | |
| 85                  90                  95                     | | |
|CAA GTC CTG CTG CAT GTG GGC TTG CCG CCG CGG GAG CCT GTG CTC AGC|  |633|
|Gln Val Leu Leu His Val Gly Leu Pro Pro Arg Glu Pro Val Leu Ser| | |
|100                 105                 110                 115 | | |

| | | | | | | | | | | | | | | | | |
|---|---|---|---|---|---|---|---|---|---|---|---|---|---|---|---|---|
| TGC | CGC | TCC | AAC | ACT | TAC | CCC | AAG | GGC | TTC | TAC | TGC | AGC | TGG | CAT | CTG | 681 |
| Cys | Arg | Ser | Asn | Thr | Tyr | Pro | Lys | Gly | Phe | Tyr | Cys | Ser | Trp | His | Leu | |
| | | | 120 | | | | 125 | | | | | 130 | | | | |
| CCC | ACC | CCC | ACC | TAC | ATT | CCC | AAC | ACC | TTC | AAT | GTG | ACT | GTG | CTG | CAT | 729 |
| Pro | Thr | Pro | Thr | Tyr | Ile | Pro | Asn | Thr | Phe | Asn | Val | Thr | Val | Leu | His | |
| | | | 135 | | | | 140 | | | | 145 | | | | | |
| GGC | TCC | AAA | ATT | ATG | GTC | TGT | GAG | AAG | GAC | CCA | GCC | CTC | AAG | AAC | CGC | 777 |
| Gly | Ser | Lys | Ile | Met | Val | Cys | Glu | Lys | Asp | Pro | Ala | Leu | Lys | Asn | Arg | |
| | | 150 | | | | | 155 | | | | | 160 | | | | |
| TGC | CAC | ATT | CGC | TAC | ATG | CAC | CTG | TTC | TCC | ACC | ATC | AAG | TAC | AAG | GTC | 825 |
| Cys | His | Ile | Arg | Tyr | Met | His | Leu | Phe | Ser | Thr | Ile | Lys | Tyr | Lys | Val | |
| | 165 | | | | | 170 | | | | | 175 | | | | | |
| TCC | ATA | AGT | GTC | AGC | AAT | GCC | CTG | GGC | CAC | AAT | GCC | ACA | GCT | ATC | ACC | 873 |
| Ser | Ile | Ser | Val | Ser | Asn | Ala | Leu | Gly | His | Asn | Ala | Thr | Ala | Ile | Thr | |
| 180 | | | | | 185 | | | | | 190 | | | | | 195 | |
| TTT | GAC | GAG | TTC | ACC | ATT | GTG | AAG | CCT | GAT | CCT | CCA | GAA | AAT | GTG | GTA | 921 |
| Phe | Asp | Glu | Phe | Thr | Ile | Val | Lys | Pro | Asp | Pro | Pro | Glu | Asn | Val | Val | |
| | | | | 200 | | | | | 205 | | | | | 210 | | |
| GCC | CGG | CCA | GTG | CCC | AGC | AAC | CCT | CGC | CGG | CTG | GAG | GTG | ACG | TGG | CAG | 969 |
| Ala | Arg | Pro | Val | Pro | Ser | Asn | Pro | Arg | Arg | Leu | Glu | Val | Thr | Trp | Gln | |
| | | | 215 | | | | | 220 | | | | | 225 | | | |
| ACC | CCC | TCG | ACC | TGG | CCT | GAC | CCT | GAG | TCT | TTT | CCT | CTC | AAG | TTC | TTT | 1017 |
| Thr | Pro | Ser | Thr | Trp | Pro | Asp | Pro | Glu | Ser | Phe | Pro | Leu | Lys | Phe | Phe | |
| | | 230 | | | | | 235 | | | | | 240 | | | | |
| CTG | CGC | TAC | CGA | CCC | CTC | ATC | CTG | GAC | CAG | TGG | CAG | CAT | GTG | GAG | CTG | 1065 |
| Leu | Arg | Tyr | Arg | Pro | Leu | Ile | Leu | Asp | Gln | Trp | Gln | His | Val | Glu | Leu | |
| | 245 | | | | | 250 | | | | | 255 | | | | | |
| TCC | GAC | GGC | ACA | GCA | CAC | ACC | ATC | ACA | GAT | GCC | TAC | GCC | GGG | AAG | GAG | 1113 |
| Ser | Asp | Gly | Thr | Ala | His | Thr | Ile | Thr | Asp | Ala | Tyr | Ala | Gly | Lys | Glu | |
| 260 | | | | | 265 | | | | | 270 | | | | | 275 | |
| TAC | ATT | ATC | CAG | GTG | GCA | GCC | AAG | GAC | AAT | GAG | ATT | GGG | ACA | TGG | AGT | 1161 |
| Tyr | Ile | Ile | Gln | Val | Ala | Ala | Lys | Asp | Asn | Glu | Ile | Gly | Thr | Trp | Ser | |
| | | | | 280 | | | | | 285 | | | | | 290 | | |
| GAC | TGG | AGC | GTA | GCC | GCC | CAC | GCT | ACG | CCC | TGG | ACT | GAG | GAA | CCG | CGA | 1209 |
| Asp | Trp | Ser | Val | Ala | Ala | His | Ala | Thr | Pro | Trp | Thr | Glu | Glu | Pro | Arg | |
| | | | 295 | | | | | 300 | | | | | 305 | | | |
| CAC | CTC | ACC | ACG | GAG | GCC | CAG | GCT | GCG | GAG | ACC | ACG | ACC | AGC | ACC | ACC | 1257 |
| His | Leu | Thr | Thr | Glu | Ala | Gln | Ala | Ala | Glu | Thr | Thr | Thr | Ser | Thr | Thr | |
| | | 310 | | | | | 315 | | | | | 320 | | | | |
| AGC | TCC | CTG | GCA | CCC | CCA | CCT | ACC | ACG | AAG | ATC | TGT | GAC | CCT | GGG | GAG | 1305 |
| Ser | Ser | Leu | Ala | Pro | Pro | Pro | Thr | Thr | Lys | Ile | Cys | Asp | Pro | Gly | Glu | |
| | 325 | | | | | 330 | | | | | 335 | | | | | |
| CTG | GGC | AGC | GGC | GGG | GGA | CCC | TGC | GCA | CCC | TTC | TTG | GTC | AGC | GTC | CCC | 1353 |
| Leu | Gly | Ser | Gly | Gly | Gly | Pro | Cys | Ala | Pro | Phe | Leu | Val | Ser | Val | Pro | |
| 340 | | | | | 345 | | | | | 350 | | | | | 355 | |
| ATC | ACT | CTG | GCC | CTG | GCT | GCC | GCT | GCC | GCC | ACT | GCC | AGC | AGT | CTC | TTG | 1401 |
| Ile | Thr | Leu | Ala | Leu | Ala | Ala | Ala | Ala | Ala | Thr | Ala | Ser | Ser | Leu | Leu | |
| | | | | 360 | | | | | 365 | | | | | 370 | | |
| ATC | | | | | | | | | | | | | | | | 1454 |
| Ile | TGAGCCCGGC | ACCCCATGAG | GACATGCAGA | GCACCTGCAG | AGGAGCAGGA | | | | | | | | | | | |

```
GGCCGGAGCT GAGCCTGCAG ACCCCGGTTT CTATTTTGCA CACGGGCAGG AGGACCTTTT       1514

GCATTCTCTT CAGACACAAT TTGTGGAGAC CCCGGCGGGC CGGGCCTGC CGCCCCCAG        1574

CCCTGCCGCA CCAAGCT                                                     1591
```

( 2 ) INFORMATION FOR SEQ ID NO:4:

( i ) SEQUENCE CHARACTERISTICS:
        ( A ) LENGTH: 372 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:4:

| | | | | | | | | | | | | | | |
|---|---|---|---|---|---|---|---|---|---|---|---|---|---|---|
| Met | Ala | Ala | Pro | Val | Pro | Trp | Ala | Cys | Cys | Ala | Val | Leu | Ala | Ala |
| 1 | | | | 5 | | | | | 10 | | | | | 15 |
| Ala | Ala | Val | Val | Tyr | Ala | Gln | Arg | His | Ser | Pro | Gln | Glu | Ala | Pro | His |
| | | | 20 | | | | 25 | | | | | 30 | | | |
| Val | Gln | Tyr | Glu | Arg | Leu | Gly | Ser | Asp | Val | Thr | Leu | Pro | Cys | Gly | Thr |
| | | 35 | | | | | | 40 | | | | | 45 | | |
| Ala | Asn | Trp | Asp | Ala | Ala | Val | Thr | Trp | Arg | Val | Asn | Gly | Thr | Asp | Leu |
| | 50 | | | | | 55 | | | | | | 60 | | | |
| Ala | Pro | Asp | Leu | Leu | Asn | Gly | Ser | Gln | Leu | Val | Leu | His | Gly | Leu | Glu |
| 65 | | | | | 70 | | | | | 75 | | | | | 80 |
| Leu | Gly | His | Ser | Gly | Leu | Tyr | Ala | Cys | Phe | His | Arg | Asp | Ser | Trp | His |
| | | | | 85 | | | | | 90 | | | | | 95 | |
| Leu | Arg | His | Gln | Val | Leu | Leu | His | Val | Gly | Leu | Pro | Pro | Arg | Glu | Pro |
| | | | 100 | | | | | 105 | | | | | 110 | | |
| Val | Leu | Ser | Cys | Arg | Ser | Asn | Thr | Tyr | Pro | Lys | Gly | Phe | Tyr | Cys | Ser |
| | | 115 | | | | | 120 | | | | | 125 | | | |
| Trp | His | Leu | Pro | Thr | Pro | Thr | Tyr | Ile | Pro | Asn | Thr | Phe | Asn | Val | Thr |
| | 130 | | | | | 135 | | | | | 140 | | | | |
| Val | Leu | His | Gly | Ser | Lys | Ile | Met | Val | Cys | Glu | Lys | Asp | Pro | Ala | Leu |
| 145 | | | | | 150 | | | | | 155 | | | | | 160 |
| Lys | Asn | Arg | Cys | His | Ile | Arg | Tyr | Met | His | Leu | Phe | Ser | Thr | Ile | Lys |
| | | | | 165 | | | | | 170 | | | | | 175 | |
| Tyr | Lys | Val | Ser | Ile | Ser | Val | Ser | Asn | Ala | Leu | Gly | His | Asn | Ala | Thr |
| | | | 180 | | | | | 185 | | | | | 190 | | |
| Ala | Ile | Thr | Phe | Asp | Glu | Phe | Thr | Ile | Val | Lys | Pro | Asp | Pro | Pro | Glu |
| | | 195 | | | | | 200 | | | | | 205 | | | |
| Asn | Val | Val | Ala | Arg | Pro | Val | Pro | Ser | Asn | Pro | Arg | Arg | Leu | Glu | Val |
| | 210 | | | | | 215 | | | | | 220 | | | | |
| Thr | Trp | Gln | Thr | Pro | Ser | Thr | Trp | Pro | Asp | Pro | Glu | Ser | Phe | Pro | Leu |
| 225 | | | | | 230 | | | | | 235 | | | | | 240 |
| Lys | Phe | Phe | Leu | Arg | Tyr | Arg | Pro | Leu | Ile | Leu | Asp | Gln | Trp | Gln | His |
| | | | | 245 | | | | | 250 | | | | | 255 | |
| Val | Glu | Leu | Ser | Asp | Gly | Thr | Ala | His | Thr | Ile | Thr | Asp | Ala | Tyr | Ala |
| | | | 260 | | | | | 265 | | | | | 270 | | |
| Gly | Lys | Glu | Tyr | Ile | Ile | Gln | Val | Ala | Ala | Lys | Asp | Asn | Glu | Ile | Gly |
| | | 275 | | | | | 280 | | | | | 285 | | | |
| Thr | Trp | Ser | Asp | Trp | Ser | Val | Ala | Ala | His | Ala | Thr | Pro | Trp | Thr | Glu |
| | 290 | | | | | 295 | | | | | 300 | | | | |
| Glu | Pro | Arg | His | Leu | Thr | Thr | Glu | Ala | Gln | Ala | Ala | Glu | Thr | Thr | Thr |
| 305 | | | | | 310 | | | | | 315 | | | | | 320 |
| Ser | Thr | Thr | Ser | Ser | Leu | Ala | Pro | Pro | Thr | Thr | Lys | Ile | Cys | Asp |
| | | | | 325 | | | | | 330 | | | | | 335 |
| Pro | Gly | Glu | Leu | Gly | Ser | Gly | Gly | Pro | Cys | Ala | Pro | Phe | Leu | Val |
| | | | 340 | | | | 345 | | | | | 350 | | |
| Ser | Val | Pro | Ile | Thr | Leu | Ala | Leu | Ala | Ala | Ala | Ala | Thr | Ala | Ser |
| | | 355 | | | | 360 | | | | | 365 | | | |
| Ser | Leu | Leu | Ile | | | | | | | | | | | |
| | 370 | | | | | | | | | | | | | |

( 2 ) INFORMATION FOR SEQ ID NO:5:

( i ) SEQUENCE CHARACTERISTICS:
        ( A ) LENGTH: 43 base pairs
        ( B ) TYPE: nucleic acid
        ( C ) STRANDEDNESS: single (D) TOPOLOGY: unknown (i i) MOLECULE TYPE: DNA (i x) FEATURE:
  (A) NAME/KEY: modifiedbase
  (B) LOCATION: 22
  (D) OTHER INFORMATION: /modbase=i
        /label=n (x i) SEQUENCE DESCRIPTION: SEQ ID NO:5:

CGCAGTGTCG ACAGCACAGC GNCACAGTCC ACAAGAAGCA CCC  43

(2) INFORMATION FOR SEQ ID NO:6:

(i) SEQUENCE CHARACTERISTICS:
    (A) LENGTH: 35 base pairs
    (B) TYPE: nucleic acid
    (C) STRANDEDNESS: single
    (D) TOPOLOGY: unknown (i i) MOLECULE TYPE: DNA (i v) ANTI-SENSE: YES (x i) SEQUENCE DESCRIPTION: SEQ ID NO:6:

GGACGCCGGC CGATTAGGGT GCGCAGGGTC CCCCG  35

PREVENTION OF ES CELL DIFFERENTIATION BY CILIARY NEUROTROPHIC FACTOR

This application is a continuation-in-part of U.S. Pat. application Ser. No. 07/801,562 filed on Dec. 2, 1991.

TABLE OF CONTENTS

1. Introduction
2. Background of The Invention
   2.1 Ciliary Neurotrophic Factor
   2.2. Ciliary Neurotrophic Factor Receptor
3. Summary of the Invention
4. Description of the Figures
5. Detailed Description of the Invention
   5.1 The CNTF/Receptor Complex
   5.2 Characteristics of the CNTF/Receptor Complex
      5.2.1. Direct $^{125}$I-hCNTF Binding Assay
      5.2.2. Signal Transduction Assay
   5.3. Utility of the CNTF/Receptor Complex
      5.3.1. In Vitro Applications
      5.3.2. In Vivo Applications
         5.3.2.1. Formation of the Active Ingredient
   5.4 CNTF, IL-6 and LIF Share Signal Transducing Components
   5.5 Uses of Common and Unique Receptor Components
      5.5.1 Use of CNTF to Prevent the Differentiation of Embryonic Stem Cells
      5.5.2 Activiation of LIF Response Cells Using CNTF/CNTFR
      5.5.3 Identification of CNTFR Antagonists
6. Example: Production of human CNTF Receptor in *E. coli*
   6.1. Materials and Methods
      6.1.1. Construction of pCP110
      6.1.2. Construction of a Vector For Expression of huCNTF 1
      6.1.3. Purification of huCNTFR1
   6.2. Results
7. Example: Formation of the CNTF/Receptor Complex
   7.1. Materials and Methods
   7.2. Results
8. Example: The CNTF/Receptor complex Promotes Differentiation of Myeloid Leukemia Cells
   8.1. Materials and Methods
      8.1.1. Cell Culture Conditions
      8.1.2. Scoring by Phenotype
   8.2 Results
9. Example: CNTF Resembles LIF in Mediating Phosphorylation of CLIP Proteins and Expression of Immediate Early Genes
   9.1. Materials and Methods
      9.1.1. Reagents
      9.1.2. Cell Structure
      9.1.3. MTT Assay, $^3$H-Thymidine Incorporation Assay and ChAT Assay
      9.1.4 RNA Isolation and Analysis
      9.1.5. Protein Isolation, Immunoprecipitation and Immunoblotting
      9.1.6 Cell Surface Biotinylation Assay
   9.2. Results
      9.2.1. CNTF and LIF mediate growth Arrest and differentiation of MAH Cells
      9.2.2. CNTF and LIF Rapidly Induce Indistinguishable Patterns of Tyrosine Phosphorylation of Cellular Proteins
      9.2.3. The Rapid and Transient Phosphorylation of CLIPs Precedes Induction of a Characteristic Immediate Early Response Gene, TIS11
      9.2.4 Downregulation of CLIP1 and CLIP2 Due to Pretreatment With CNTF or LIF Cannot Be Reversed by CNTF or LIF Addition
      9.2.5 Expression of Clips On The Cell Surface
10. Example: Characterization of CLIP2
   10.1 Clip2 Is Identical to gp130
   10.2 Anti-gp 130 Antibody Selectively Blocked Tyrosine Phosphorylation of Clips and tis 11 Induction
   10.3 gp130 Is Expressed Ubiquitously Whereas CNTFR Expression Is More Limited
11. Example: Response of ES Cells to CNTF
   11.1 ES Cell Culture with LIF and CNTF
   11.2 RNA Analysis
   11.3 CNTF Binding to ES Cells
   11.4 Results
      11.4.1 ES Cell Culture
      11.4.2 Expression of CNTFR in ES Cells
      11.4.3 Binding of CNTF to ES Cells
      11.4.4 Induction of tis 11 by CNTF and LIF in ES Cells
References
Claims

1. INTRODUCTION

The present invention provides for substantially purified cell-free CNTF/receptor complex and to related hybrid or mutant proteins or peptides that may, in alternative embodiments of this invention, be used to promote or antagonize cell proliferation and/or differentiation, and that may be used in methods for diagnosing and/or treating disorders of cell proliferation and/or differentiation. The invention further provides for the interaction of such complexes with receptor components that are shared by IL-6, LIF and CNTF signal transduction pathways.

2. BACKGROUND OF THE INVENTION

2.1. Ciliary Neurotrophic Factor

Ciliary neurotrophic factor (CNTF), as its name implies, is a protein that is specifically required for the survival of embryonic chick ciliary ganglion neurons in vitro [Manthorpe et al., J. Neurochem. 34:69–75 (1980)]. CNTF has been cloned and synthesized in eukaryotic as well as bacterial expression systems, as described in International application No. POT/U.S. 90/05241, filed Sep. 14, 1990 by Sendtner et al., incorporated by reference in its entirety herein.

Over the past decade, a number of biological effects have been ascribed to CNTF in addition to its ability to support the survival of ciliary ganglion neurons. CNTF is believed to induce the differentiation of bipotential glial progenitor cells in the perinatal rat optic nerve and brain [Hughes et al., Nature 335:70–73 (1988)]. Furthermore, it has been observed to promote the survival of embryonic chick dorsal root ganglion sensory neurons [Skaper and Varon, Brain Res. 389:39–46 (1986)].

Several novel activities of CNTF have also been discovered, including its ability to support the survival and differentiation of motorneurons and hippocampal neurons, and to increase the rate of hippocampal astrocyte proliferation (International Application No. POT-/US 90/05241, supra).

2.2. Ciliary Neurotrophic Factor Receptor

The CNTF receptor (CNTFR or CNTFRα) has been cloned and expressed in eukaryotic cells, as described in U.S. Patent application Ser. No. 07/700,677, entitled "The Ciliary Neurotrophic Factor Receptor," filed May 15, 1991 by Davis, et al. and International application No. PCT/U.S. 91/03896, filed Jun. 3, 1991, incorporated by reference in their entirety herein.

The sequence of CNTFR reveals that, unlike most receptors which contain an extracellular domain, a hydrophobic transmembrane domain, and a cytoplasmic domain, CNTFR does not appear to have a cytoplasmic domain. Additionally, the transmembrane hydrophobic domain is proteolytically processed, with the mature form of CNTFR becoming anchored to the cell surface by an unconventional linkage, referred to as a glycophosphatidyl inositol (GPI)linkage (Id.). GPI-linked proteins such as CNTFR may be released from the cell surface through cleavage of the GPI anchor by the enzyme phosphatidylinositol-specific phospholipase C. Of other known receptor sequences, CNTFR is related to a number of receptors, referred to herein as the CNTF/IL-6/LIF receptor family, including IL-6, LIF, G-CSF and oncostatin M (OSM)[Bazan, Neuron Z:197-208 (1991); Rose and Bruce, Proc. Natl. Acad. Sci. 88: 8641-8645, (1991)], but appears to be most closely related to the sequence of the receptor for IL-6. However, IL-6 has not been shown to be a GPI-linked protein [e.g., Taga, et al.,, Cell 58:573-581 (1989); Hibi, et al.,, Cell 63:1149-1157 (1989)].

LIF, G-CSF and OSM are all broadly acting factors that, despite having unique growth-regulating activities, share several common actions with IL-6 during hemopoiesis as well as in other processes. For example, all can inhibit the proliferation and induce the differentiation of the murine myeloid leukemia cell line, M1 [Rose and Bruce, Proc. Natl. Acad. Sci. 88:8641-8645 (1991)]. The use of related receptor systems may provide a basis for the similar biological actions of these hemopoietic cytokines - G-CSF, IL-6, OSM and LIF all have receptor components that are structurally homologous to gp130 [Fukunaga eta!., EMBO J. 10: 2855-2865 (1991); Gearing et al., EMBO J. 10:2839-2848 ( 1991); Gearing et al. Science 255:1434 (1992)]. Furthermore, recent work reveals that LIF induces similar tyrosine phosphorylations and gene activations as IL-6 [Lord et al., Mol. Cell. Biol.11:4371-4379 (1991).

CNTFR mRNA expression has been observed in the central nervous system, sciatic nerve, adrenal tissue, and in muscle. This indicates that CNTF possesses not only neurotrophic activity, but other activities as well, including myotropic activity, which may explain the involvement of both the central nervous system and muscle in certain clinical syndromes.

It would be reasonable to infer that, in nature, the spectrum of activity of CNTF is largely restricted to cells that express the CNTFR. In light of the survival promoting and cellular differentiation effects that CNTF has been shown to impart, it would be advantageous if such activity could be extended to target cells that do not express the CNTF receptor.

The identification of hemopoietic factors that share receptor components with CNTF would enable the utilization of CNTF and its specific receptor components for activation of targeted cells that are normally responsive to such hemopoietic factors.

3. SUMMARY OF THE INVENTION

The present invention relates to a cell-free CNTF/receptor complex. It is based, in part, on the discovery that cell-free CNTF/receptor complex is biologically active on a broader spectrum of cell types than those that express the CNTF receptor. In a specific embodiment of the invention, the CNTF/receptor acts as a differentiation factor in cell types that express receptors belonging to the CNTF/IL-6/LIF receptor family.

The present invention is further based on the ability of CNTF and cell-free CNTFR to form a stable, biologically active CNTF/receptor complex under normal physiological buffer conditions. In one specific nonlimiting embodiment of the invention, equimolar amounts (e.g., 80 raM) of recombinant CNTF and CNTFR are mixed under normal physiological buffer conditions (100 mM Tris-Hcl, 50 mM NaCl, pH 8.0) to form a stable, biologically active CNTF/receptor complex. This CNTF/receptor complex may be purified via gel filtration and utilized in assays described infra.

The invention further provides for hybrid or mutant proteins related to the CNTF/receptor complex which function as either agonists or antagonists of cellular differentiation factors. For example, in one specific embodiment, a hybrid or mutant CNTFR may be unable to bind CNTF but be capable of signal transduction. This hybrid or mutant may be utilized to promote or enhance the differentiation, proliferation, growth or survival of cells that are responsive to the CNTF/receptor complex, including cells that express receptors that are members of the CNTF/IL-6/LIF receptor family independent of CNTF levels. In an alternative, non-limiting embodiment, a mutant receptor may exhibit an increased binding affinity for CNTF, but be unable to effectively induce signal transduction. Such a mutant may be useful in binding to and neutralizing CNTF without eliciting secondary effects on cell differentiation.

The invention also provides for in vitro or in vivo diagnostic methods and for assay systems for use in testing target cells for sensitivity to a particular treatment involving the CNTF/receptor.

The invention further provides for therapeutic methods for treating not only CNTF-related disorders but also disorders of differentiation and/or proliferation related to any target cell which is responsive to cell-free CNTF/receptor complex or related compounds.

The present invention also provides for a method of producing substantially purified, biologically active CNTFR or related molecules in bacteria.

The present invention is also based on the discovery that CNTF and LIF act on neuronal cells via the IL-6 transducing receptor component gp130 and a gp130-like second receptor component(referred to as LIFβ), together which, when bound to CNTF and CNTFR initiate signal transduction using a signalling pathway comparable to IL-6. Based on this discovery, the invention provides for the utilization of CNTF and CNTFR to induce a response in cells that are normally responsive to LIF or IL-6 (presumably because they express gp130 and LIFRβ).

The present invention also provides for a method of targeting cells with CNTFR(CNTFRα) so that CNTF can be used to selectively initiate signal transduction in such cells.

4. DESCRIPTION OF THE FIGURES

FIGS 1A-1B. Nucleic acid sequence (SEQ ID NO:1) of human CNTF and the deduced amino acid sequence (SEQ ID NO:2).

FIGS. 2A-2B. Nucleic acid sequence (SEQ ID NO:3) of CNTFR encoding cDNA and deduced amino acid sequence (SEQ ID NO:4).

FIG. 3. DNA sequences of the PCR primers used in the construction of pRPN151. Small characters indicate positions at which the DNA sequence was modified in order to optimize expression without modification of the protein sequence. Sense:(SEQ ID NO:5) Anti Sense:(SEQ ID NO:6).

FIG. 4. Physical and restriction map of pRPN151. The length of the plasmid in base pairs (bp), the positions of a few unique restriction sites, as well as the physical location of the huCNTRF1 (dotted bar) and the beta lactamase (solid bar) genes are shown.

Figure 5A:
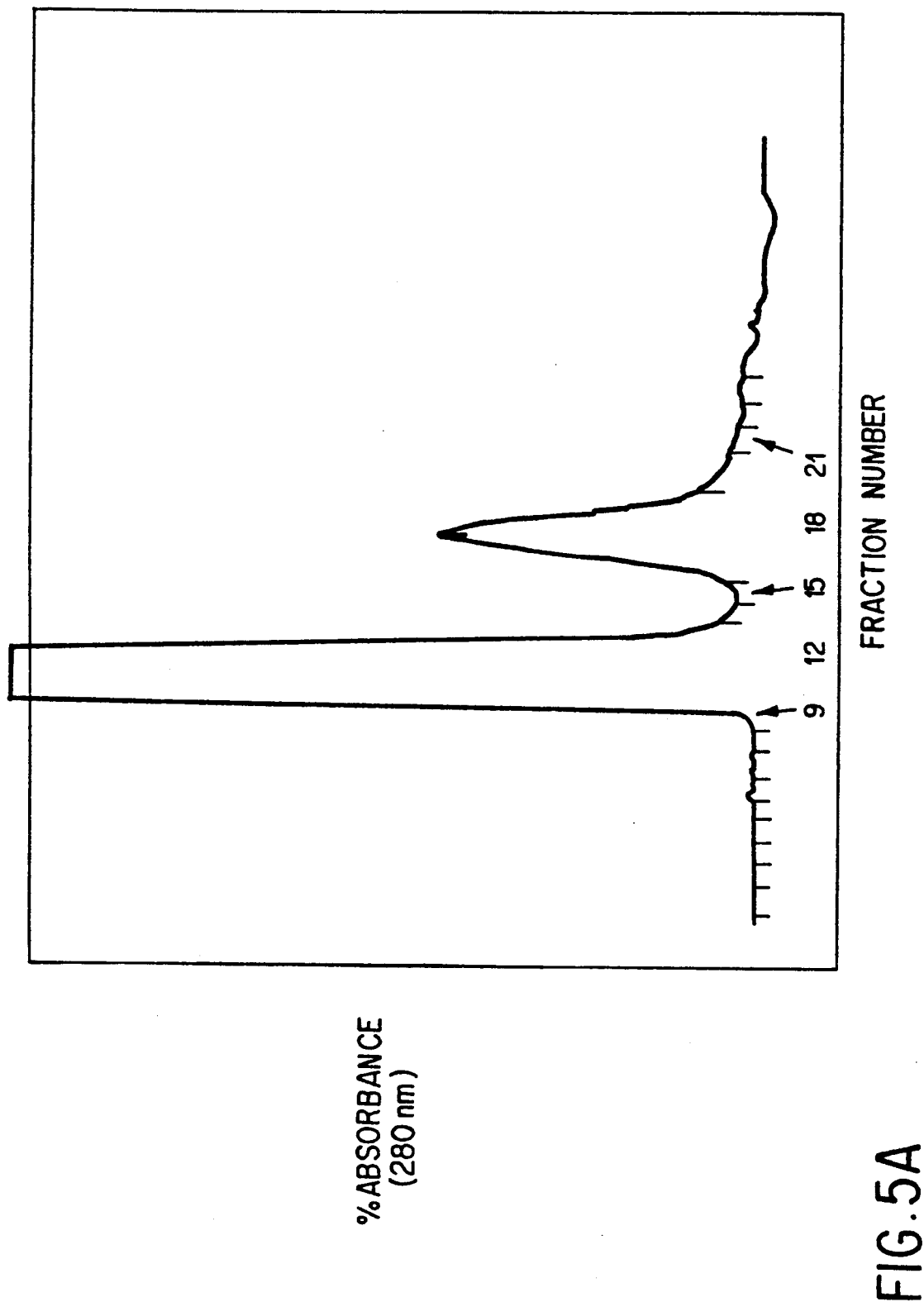
Figure 5B:
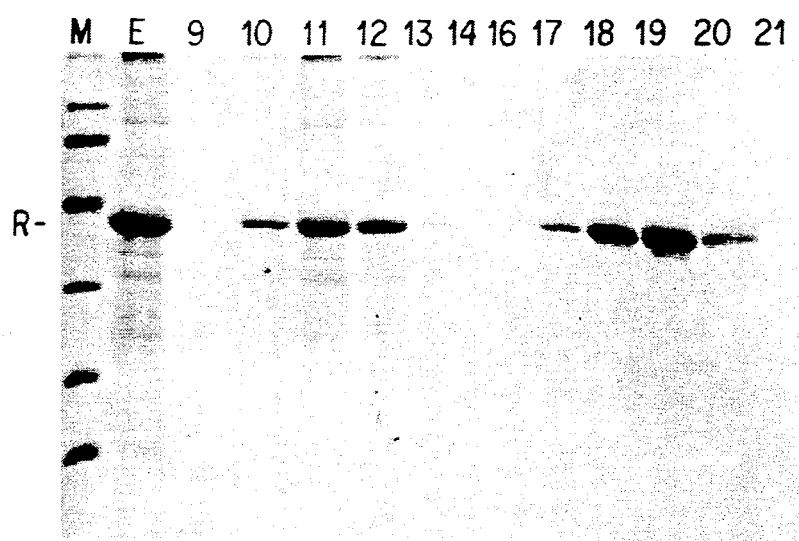

FIGS. 5A-5B. Isolation of active receptor by gel filtration. (A) Elution profile of an S100-HR column, monitored by absorbance at 280 nm. Nucleic acids contribute approximately 50% to the absorbance of the major peak but less than 10% to the smaller one. (B) Proteins eluting in fractions 9-14 (20 $\mu$l per lane) and 16-21 (200 $\mu$l per lane), were analyzed by SDS-PAGE. Total protein extract applied to the column (lane E)is also shown, along with size markers of 14, 21, 31, 45, 66 and 90 kD (lane M). R-, indicates the position of the receptor band at 40 kD.

Figure 6:
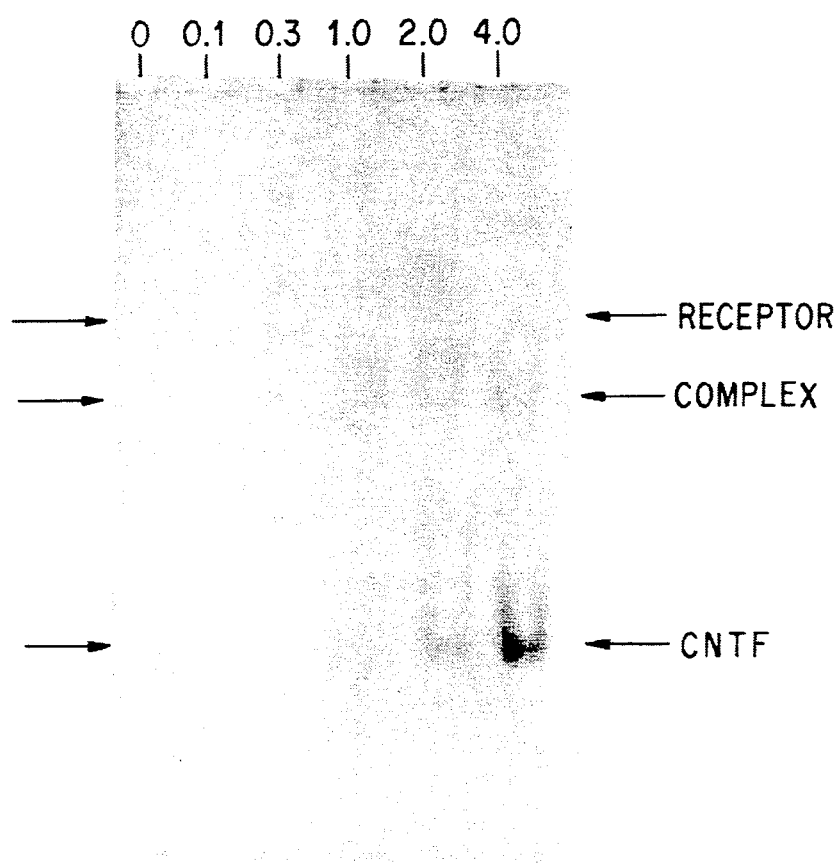

FIG. 6. Receptor ligand complex formation by native PAGE. A constant amount of receptor (1 ug) was mixed with the indicated amounts (in ug) of rat CNTF and analyzed by native PAGE. The positions of the bands corresponding to CNTFR, CNTF, and the CNTF/receptor complex are indicated.

FIGS. 7A-7D. Growth of MAH cells following treatment with CNTF, LIF and FGF. A. MAH cells were plated at a density of 250 K/35 mm dish, treated with CNTF (10 ng/ml), or LIF (1 ng/ml) for 4 days in culture. At the end of the culture period, the number of phase-bright cells were counted. B. MAH cells were plated at a density of 6K/6mm well, treated with CNTF(10 ng/ml), or LIF(1 ng/ml) for 1-4 days, and the number of vital cells were assayed using MTT dye. C. Various concentrations of CNTF, LIF and FGF were added to MAH cells. The culture period was continued for 4 days for CNTF and LIF, and for 3 days for FGF prior to 3H-thymidine incorporation assay. Plating density was at 6K/6mm well for CNTF and LIF, and 40 K/16 mm well for FGF.

Figure 8A:
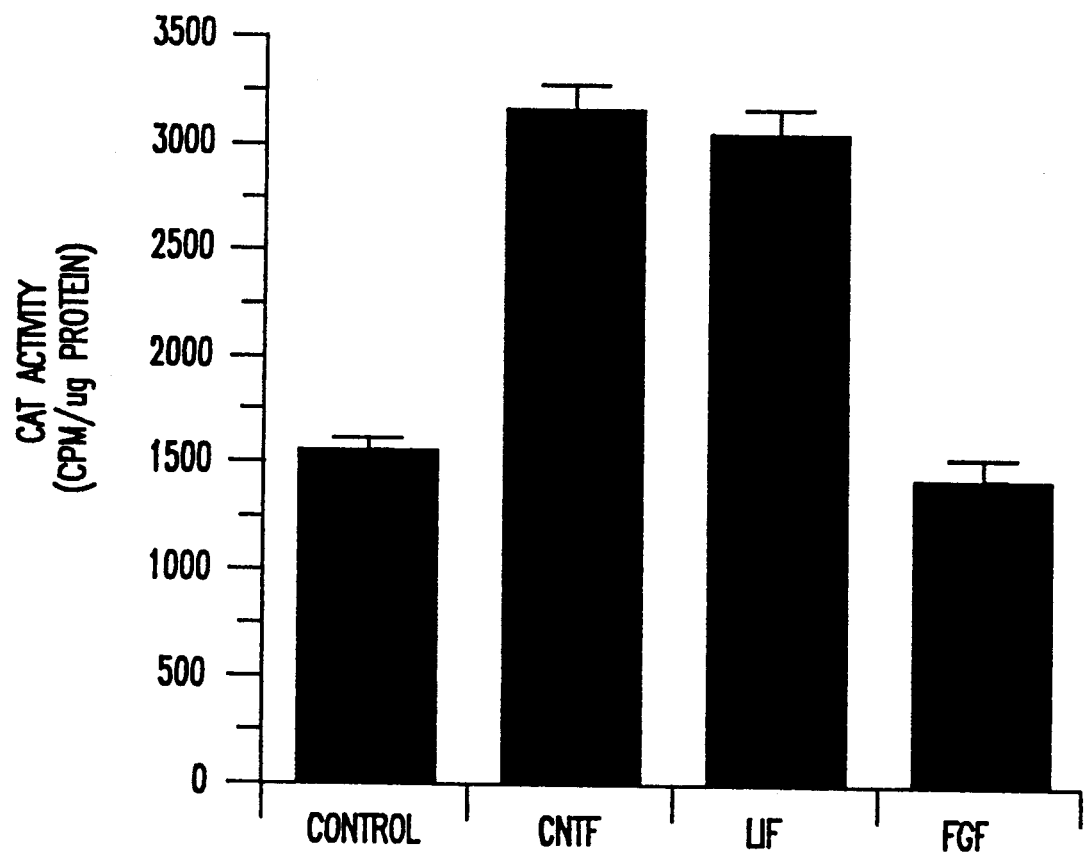

FIGS. 8A-8B. CNTF affects neuronal differentiation. A. MAH cells were treated with CNTF (10 ng/ml), LIF (1 ng/ml) or FGF (10 ng/ml) for 48hr, followed by measurement of CAT activity. B. MAH cells were treated with CNTF (10 ng/ml) for 24hr. Total RNA was prepared and subjected to northern analysis using a CNTFR probe and a GAPDH probe. The transcript sizes for CNTFR and GAPDH were 2kb.

Figure 9A:
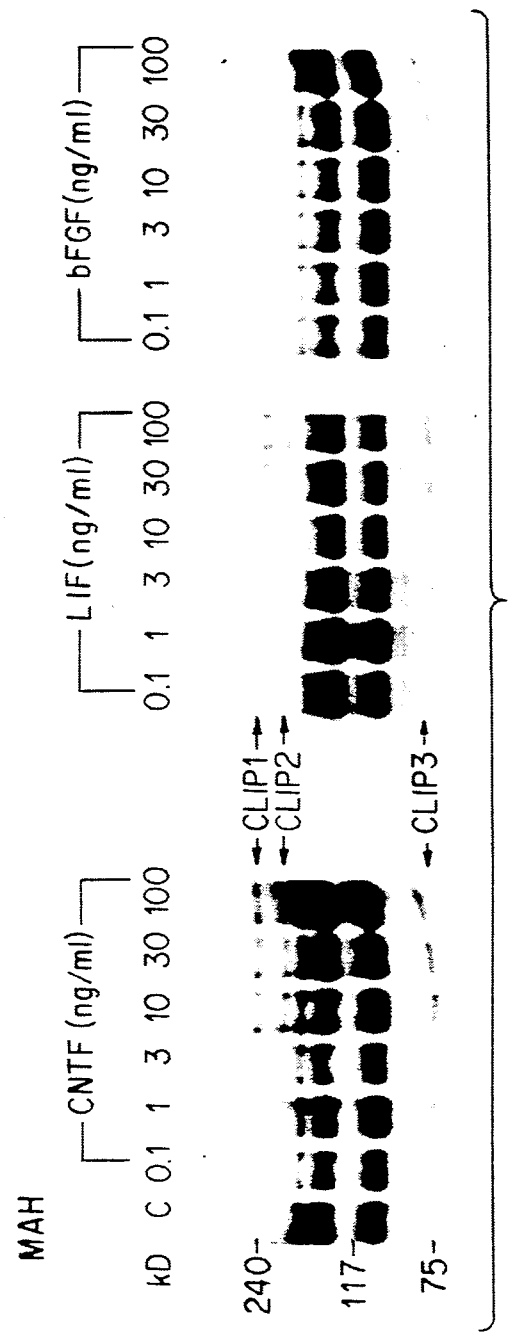
Figure 9C:
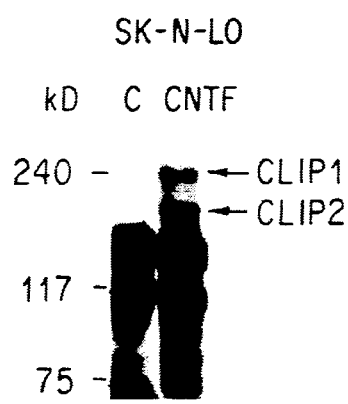

FIGS. 9A-9C. Dose-dependent tyrosine phosphorylation of proteins in response to CNTF, LIF and FGF. Total cell lysates were prepared from MAH cells (A) or EW-1 cells (B) following a 5 rain treatment with various concentrations (0.1-100 ng/ml) of CNTF, LIF or FGF. Lysates were immunoprecipitated with anti-phosphotyrosine antibody, electrophoresed and immunoblotted with antiphosphotyrosine antibody as described in Experimental procedures. (C) SK-N-LO cells were treated with 50 ng/ml of CNTF for 5 or 15 rain prior to anti-phosphotyrosine immunoprecipitation and blotting as described above.

Figure 10A:
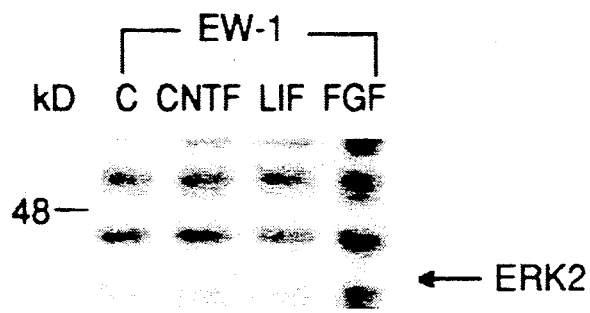
Figure 10B:
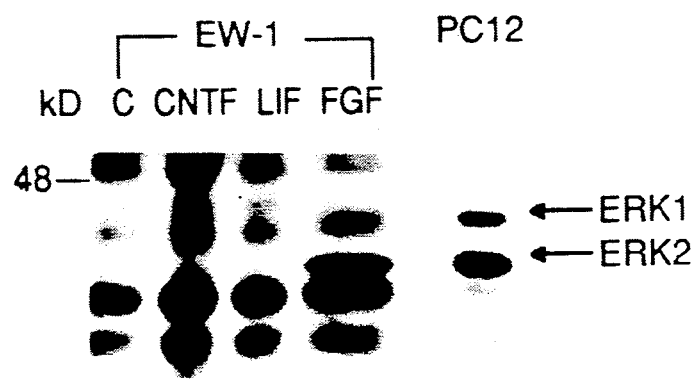
Figure 10C:
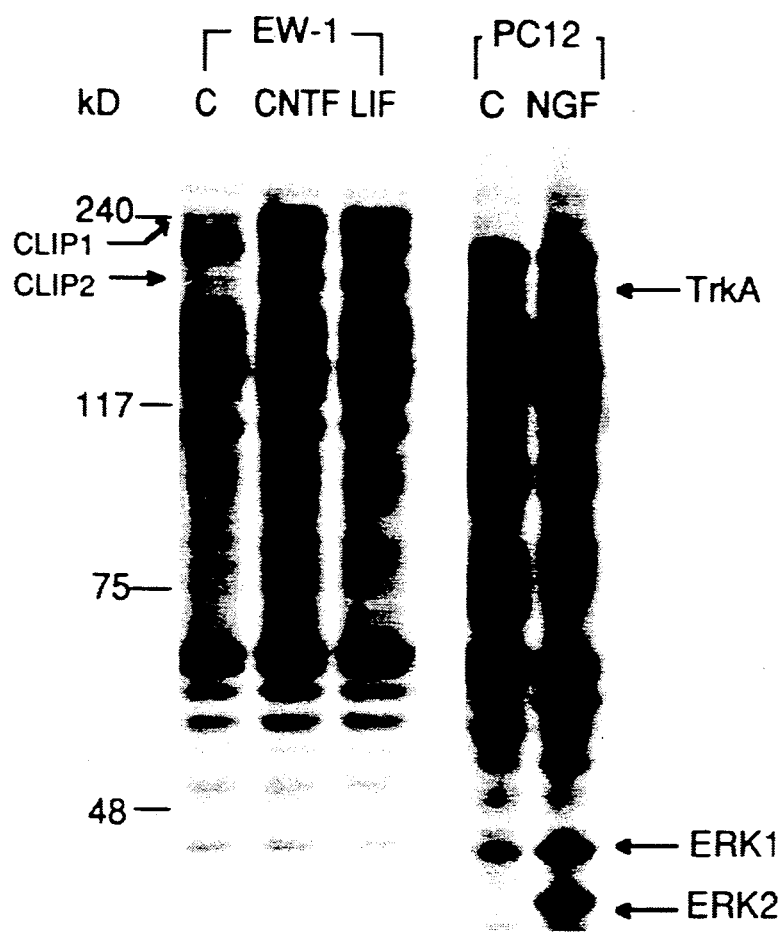

FIGS. 10A-10C. Unique protein tyrosine phosphorylation patterns of CNTF, or LIF treated cells compared to FGF or NGF treated cells. A. EW-1 cells were treated with 50 ng/ml of CNTF, LIF or FGF for 5 min. Total cell lysates were immunoblotted with anti-phosphotyrosine antibody. B. Total cell lysates prepared from EW-1 cells following treatment with 50 ng/ml of CNTF, LIF or FGF were immunoprecipitated using anti-phosphotyrosine antibody. As controls, ERK1 and ERK2 were precipitated from PC12 cell lysates using ERK-specific antibody. Immunoblotting was performed with ERK antibody. C. Total cell lysates were prepared from EW-1 cells treated with CNTF (50 ng/ml) or LIF (50 ng/ml) and PC12 cells treated with NGF (50 ng/ml). Lysates were electrophoresed and immunoblotted with anti-phosphotyrosine antibody.

Figure 11A:
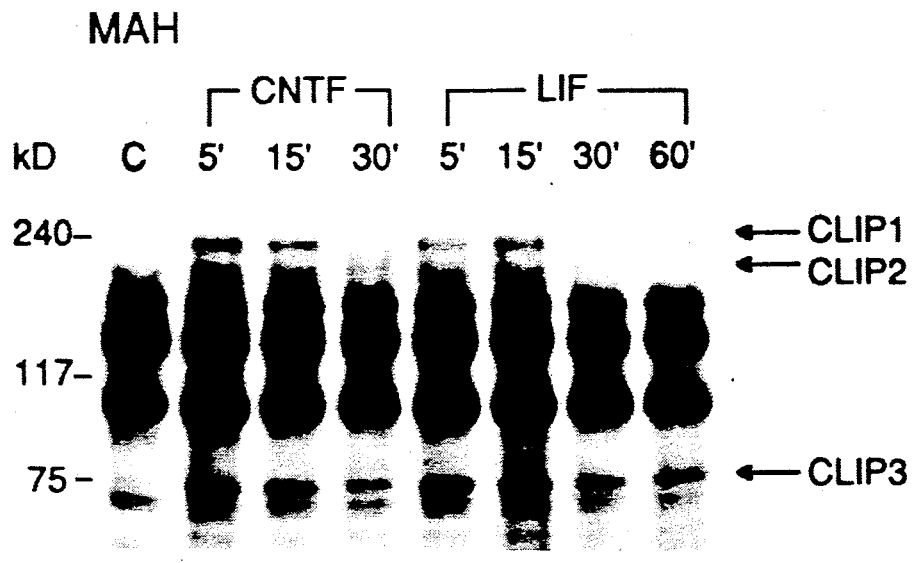
Figure 11B:
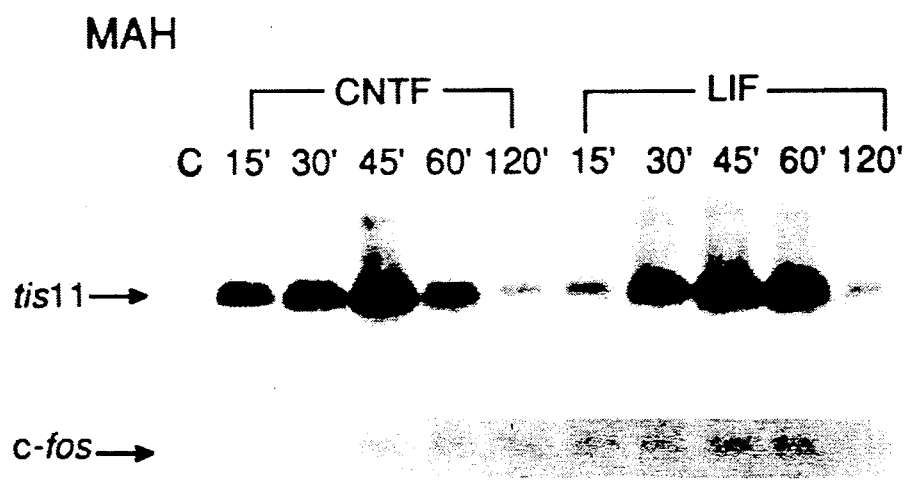
Figure 11C:
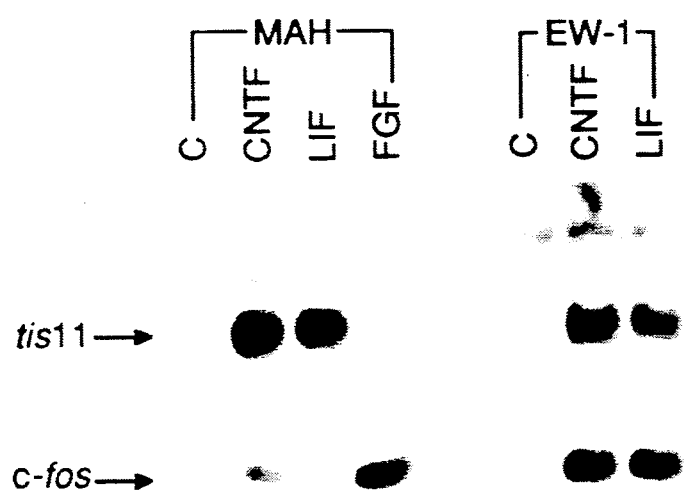

FIGS. 11A-11C. Time course comparison of protein tyrosine phosphorylation changes to tis11 induction in response to CNTF and LIF in MAH cells. A. MAH cells were treated with 50 ng/ml of CNTF or LIF for 5-60 min. Total cell lysates were immunoprecipitated and immunoblotted with anti-phosphotyrosine antibody as described in FIG. 3. B. MAH cells were similarly treated with CNTF or LIF for 15-120 min. Total RNA were prepared, fractionated by formaldehyde agarose gel electrophoresis and hybridized to tis11 and c-fos DNA probes as described in Experimental procedures. C. MAH or EW-1 cells were treated with CNTF (50 ng/ml), LIF (50 ng/ml) or FGF for 30 min. Total RNA were prepared, and expression of tis11 and c-fos were analyzed as above. The transcript sizes for tis11 and c-fos were 2.3 and 2kb, respectively.

Figure 12:
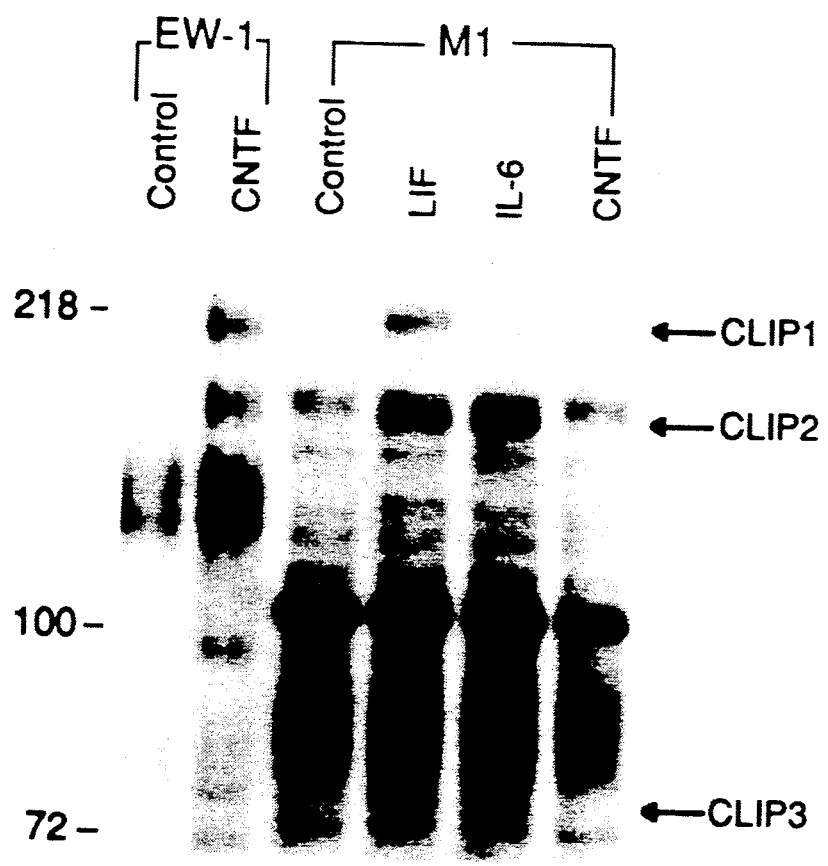
Figure 13A:
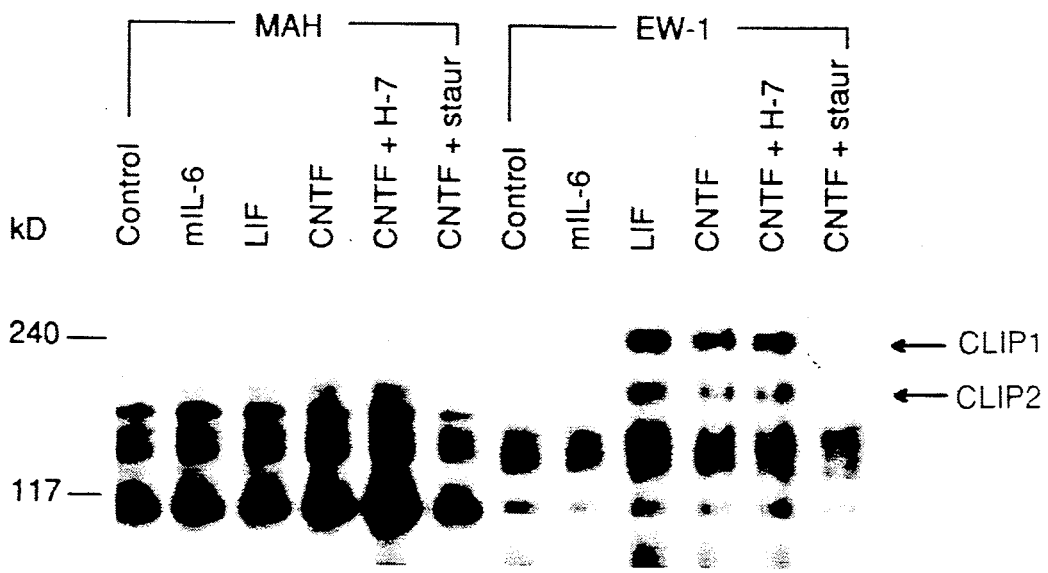
Figure 13B:
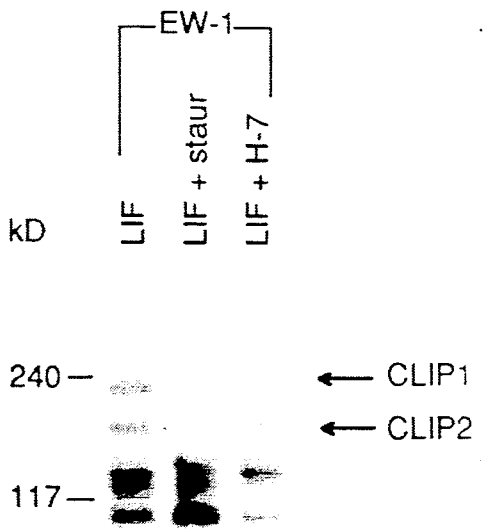

FIG. 12. Comparison of tyrosine phosphorylation changes in response to CNTF, LIF or IL-6 in EW-1 and M1 cells. EW-1 or M1 cells were treated with CNTF (50 ng/ml), LIF (50 ng/ml) or mIL-6 (100 ng/ml) for 5 minutes. Total cell lysates were immunoprecipitated and immunoblotted with antiphosphotyrosine antibody as described supra.

FIGS. 13A-13D. Effects of protein kinase inhibitors on CNTF- and LIF-induced protein tyrosine phosphorylation and tis11 gene expression MAH (A) or EW-1 (B) cells were treated with protein kinase inhibitors H-7 (40 ug/ml) or staurosporine (100 ng/ml) for 15 minutes prior to addition of GNTF (50 ng/ml), LIF (50 ng/ml) or mIL-6 (100 ng/ml). Total cell lysates were immunoprecipitated and immunoblotted with anti-phosphotyrosine antibody as described supra. To examine the effects of protein kinase inhibitor on tis11 induction, MAH(C) or MI(D) cells were treated with protein kinase inhibitors H-7 (40 ug/ml) for 30 rain prior to addition of CNTF (50 ng/ml), LIF (50 ng/ml) or mIL-6 (100 ng/ml). Total RNA were prepared and subjected to northern analysis using a tis11 probe.

Figure 14A:
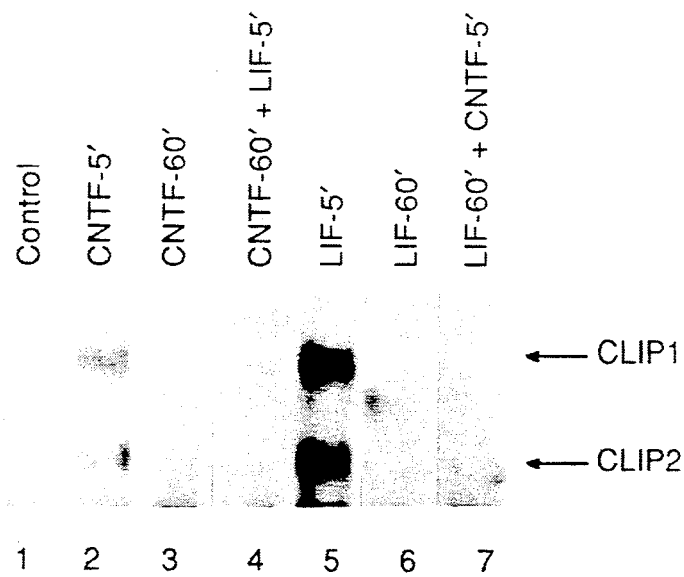
Figure 14B:
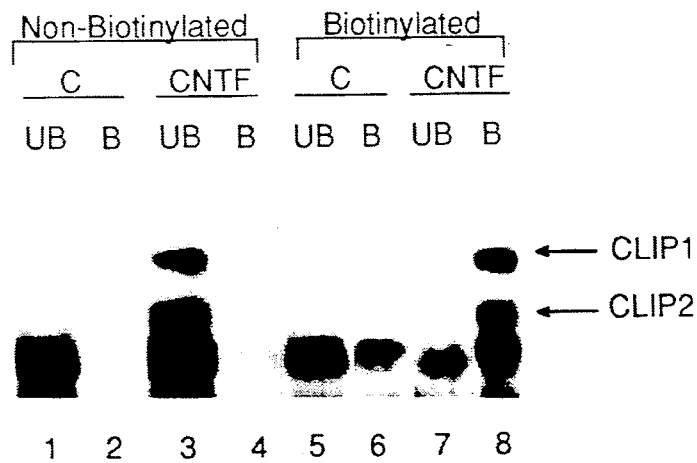
Figure 14C:
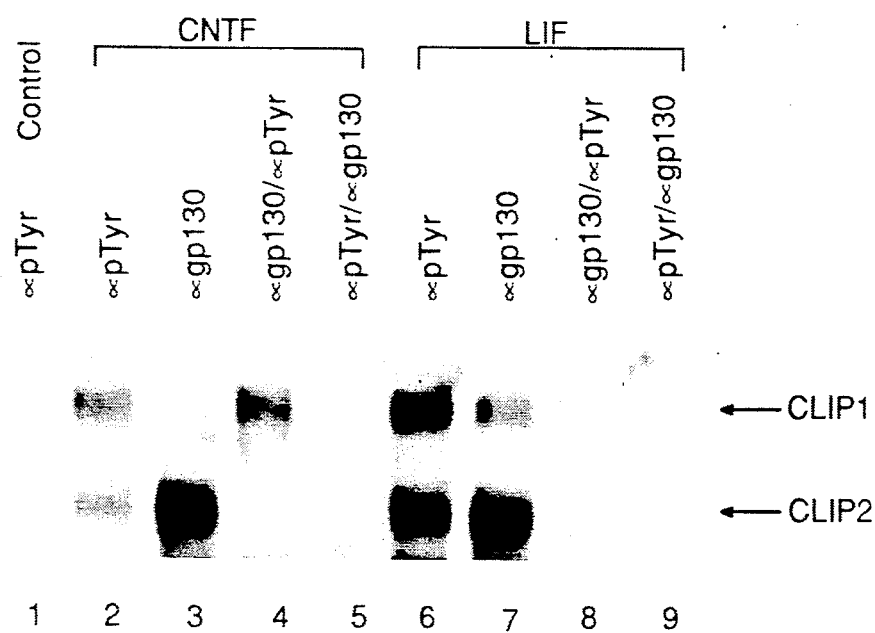

FIGS. 14A-14C. The CLIPs are co-regulated by CNTF and LIF (A), are on the cell surface (B), and one of the CLIPs (CLIP2)is gp130. A. CLIP1 and CLIP2 are co-regulated by CNTF and LIF. EW-1 cells were treated for five or 60 minutes with either CNTF (50 ng/ml) or LIF (50 ng/ml), as indicated; after the 60 minute timepoints either additional CNTF (lanes 3 and 7) or LIF (lanes 4 and 6) were added to the cells for five additional minutes. Total cell lysates were then immunoprecipitated and immunoblotted with anti-phosphotyrosine antibody. B. Biotinylation assay reveals that CLIP1 and CLIP2 are on the cell surface. EW-1 cells were surface biotinylated as described herein. The figure shows the anti-phosphotyrosine immunoblot for control (C) or CNTF stimulated (CNTF) cells that were subsequently biotinylated or left non-biotinylated before separation into unbound (UB) or bound (B) fractions on streptavidin-agarose. C. CLIP2 is gp130. The figure shows the anti-phosphotyrosine immunoblot of lysates from control (C) or CNTF/LIF stimulated EW-1 cells that were immunoprecipitated with the anti-phosphotyrosine antibody ($\alpha$pTyr) or the gp130-specific antibody ($\alpha$gp130). The immunoprecipitating antibodies were either used individually or in sequential manner, as indicated.

Figure 15:
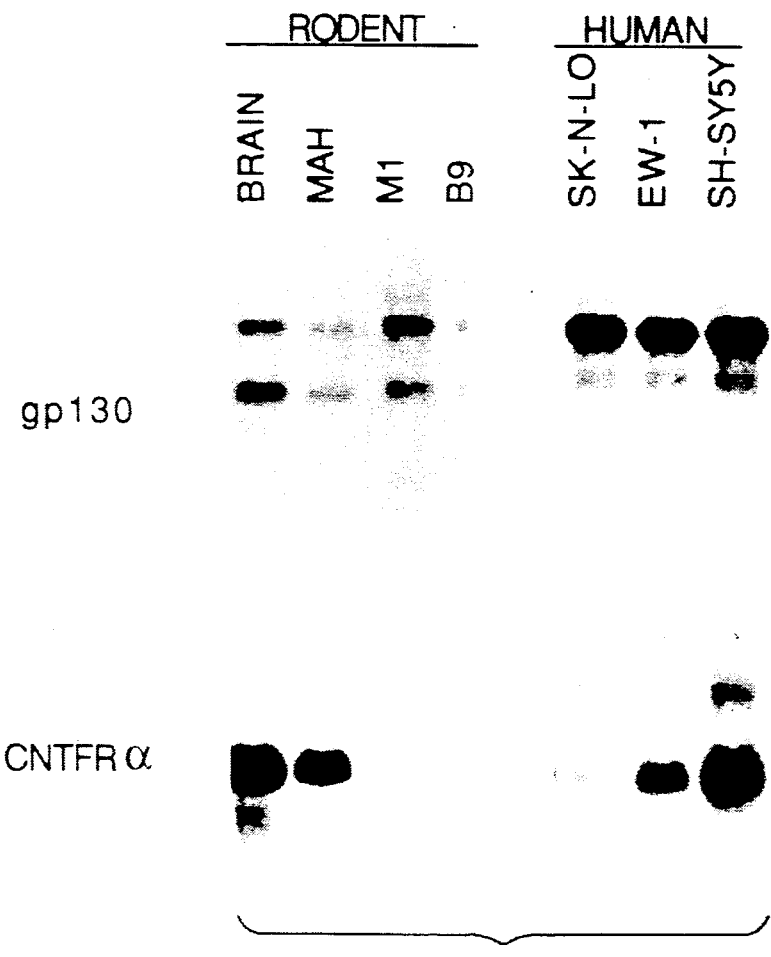

FIG. 15. Ubiquitous distribution of gp130 mRNA contrasts with restricted neuronal distribution of CNTFR$\alpha$mRNA. Total RNA was prepared from the indicated lines and subjected to northern analysis using either a human gp130 cDNA probe (top panels), or a rat CNTFR eDNA probe (bottom panels); the weaker hybridization to the rodent lines with the gp130 probe is due to poor cross-species hybridization. SH-SYSY, neuroblastoma; EW-1, ewing's sarcoma; SK-N-LO, neuroepithelioma; MAH, sympathoadrenal progenitor; M1, myeloid progenitor; Bg, IL-6 dependent B cell hybridoma that does not respond to CNTF.

Figure 16:
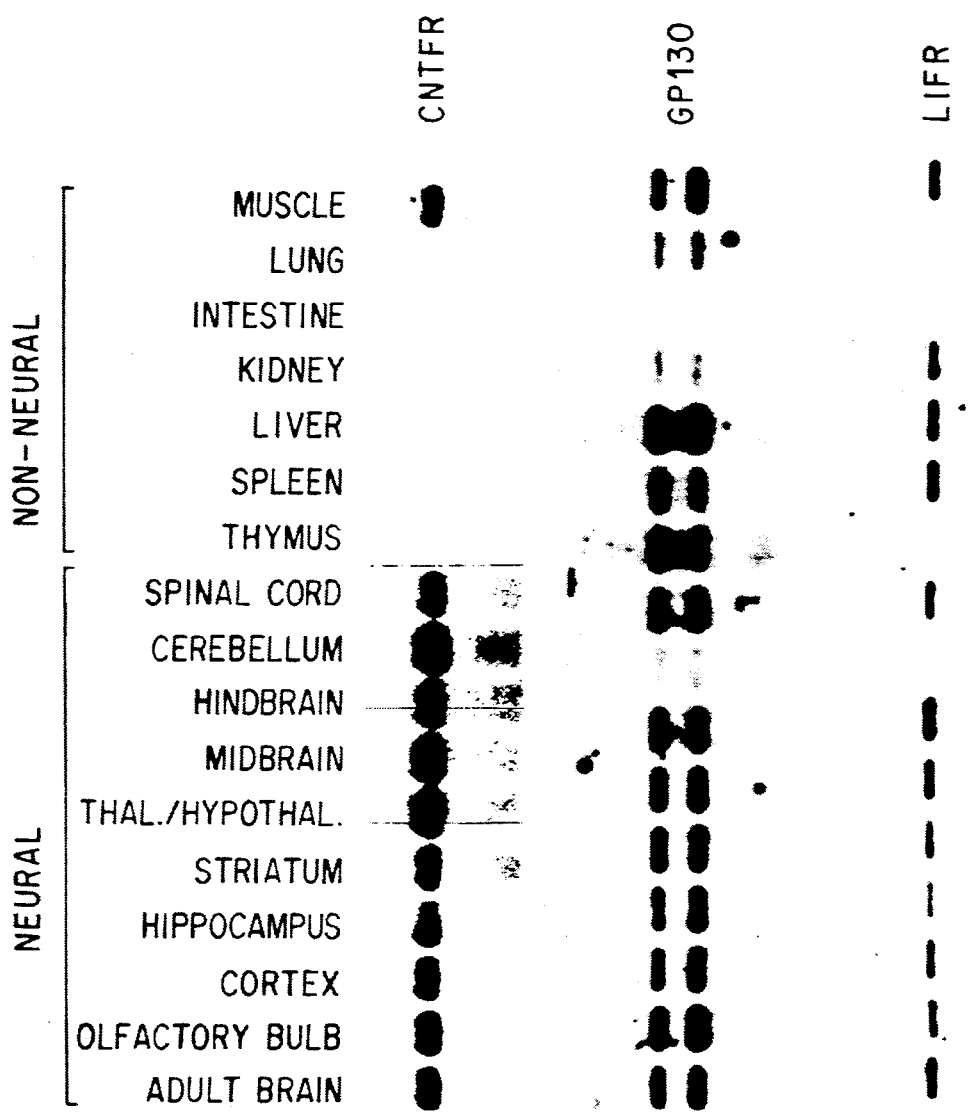

FIG. 16. Ubiquitous distribution of gp130 mRNA in tissues. Total RNA and northern analysis was conducted as in FIG. 15.

Figure 17A:
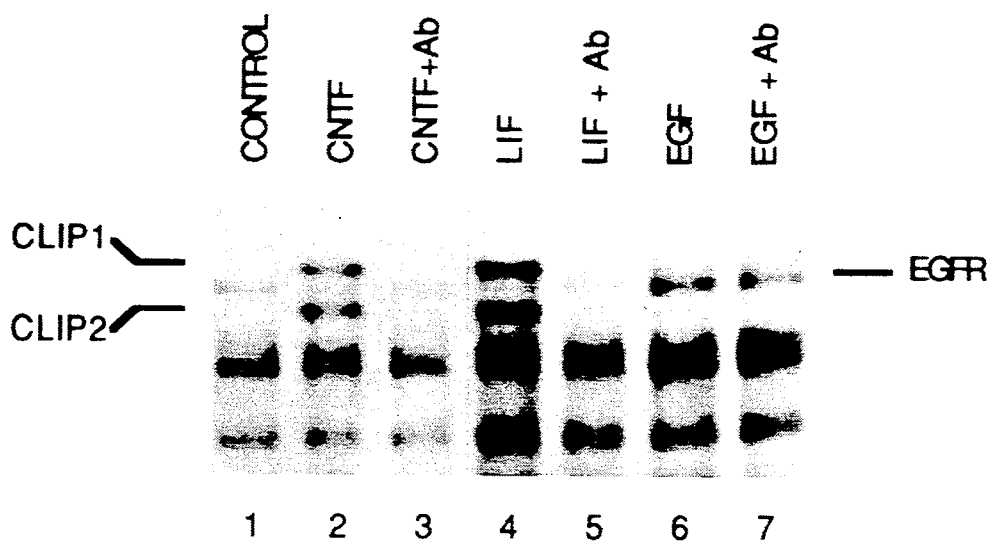
Figure 17B:
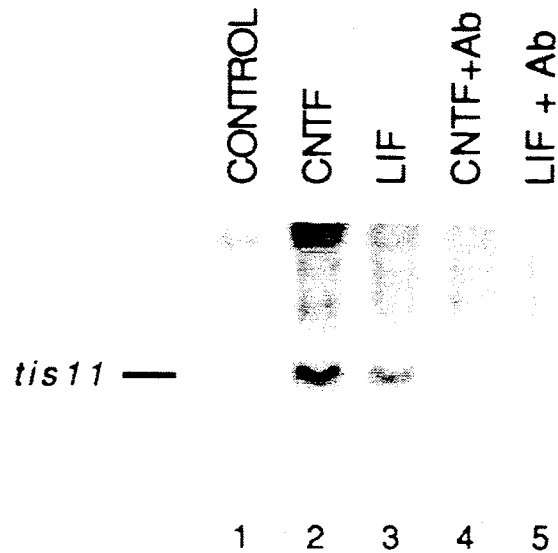
Figure 18A:
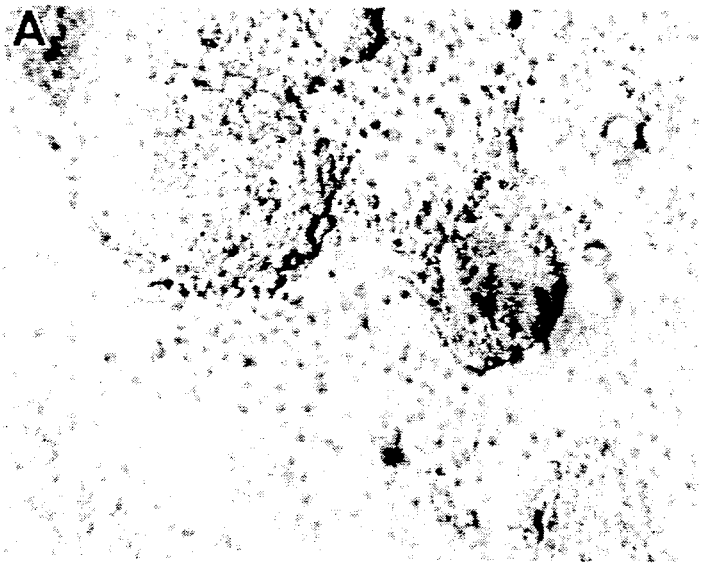
Figure 18B:
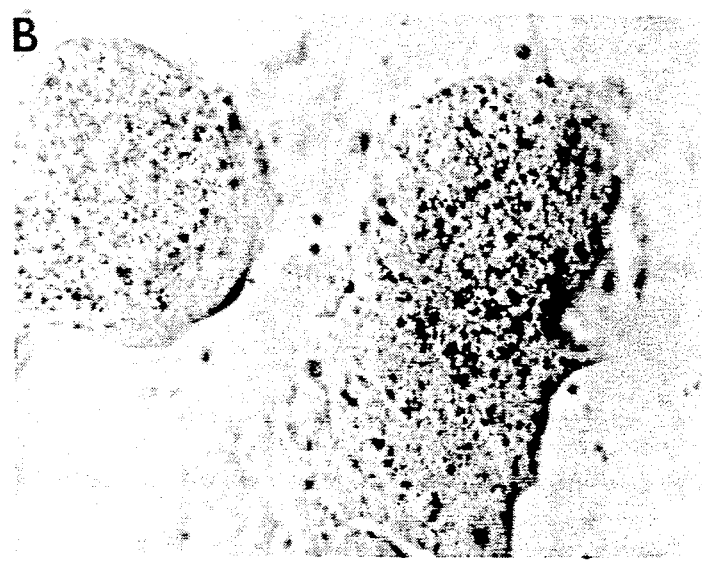
Figure 18C:
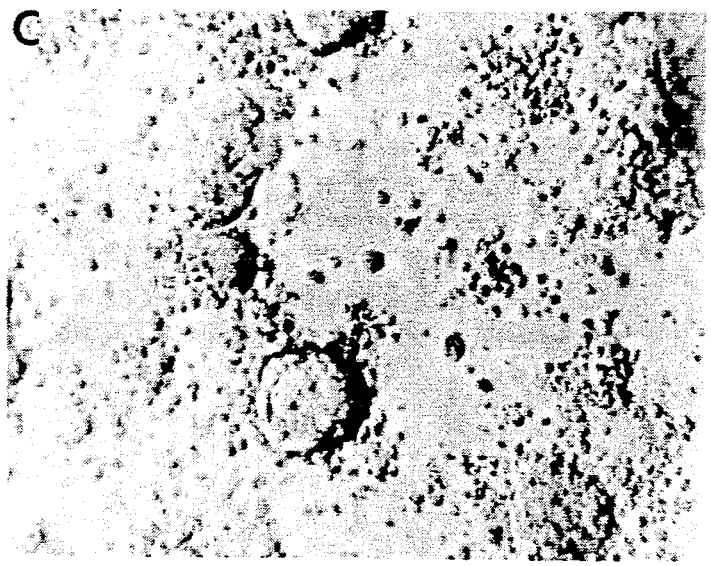
Figure 18D:
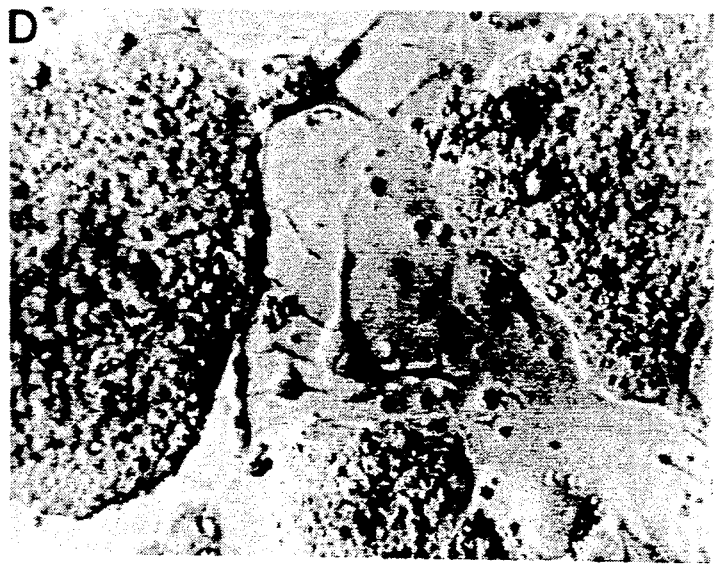

FIGS. 17A–17B. gp130 blocking antibodies prevent CNTF/LIF induced tyrosine phosphorylations and gene inductions. Antibodies were examined for their ability to block tyrosine phosphorylations induced by CNTF and LIF in EW-1 cells. Tyrosine phosphorylations of CLIP 1 and CLIP2 (panel A), as well as tis 11 gene expression induced by CNTF or LIF (panel B) were both completely blocked by anti-gp130.

FIGS. 18A–18D. Effect of LIF and CNTF on ES cells. ES cells maintained in the absence of feeder cells, but in the presence of LIF (10–20ng/ml) remained as undifferentiated, compact colonies of small cells. Lower concentrations of LIF (less than 10 ng/ml) resulted in the differentiation of the ES cells over a period of 2–7 days, as evidenced by the presence of endoderm-like cells and large, flat cells, with some cell death occurring (Panel 18A). ES cells grown on gelatin plates with 5 pg/ml to 10 ng/ml CNTF, resulted in differentiation and some cell death. Concentrations of CNTF greater than 10 ng/ml up to 50 ng/ml CNTF maintained ES cells as small compact colonies of cells (Panel 18B). ES cells maintained in the absence of either LIF or CNTF appeared endoderm-like or large and flat over a period of 2–7 days (Panel 18C).

Figure 19:
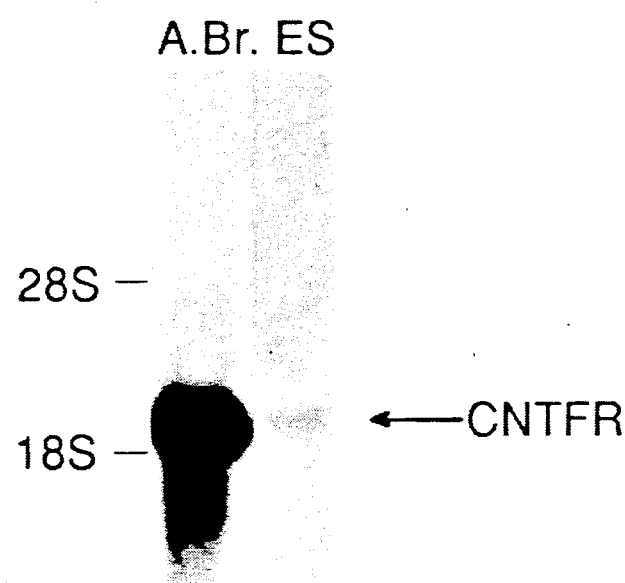

FIG. 19. Expression of CNTFR in ES cells. Northern analysis of RNA from ES cells and rat brain indicating expression of CNTFR.

Figure 20A:
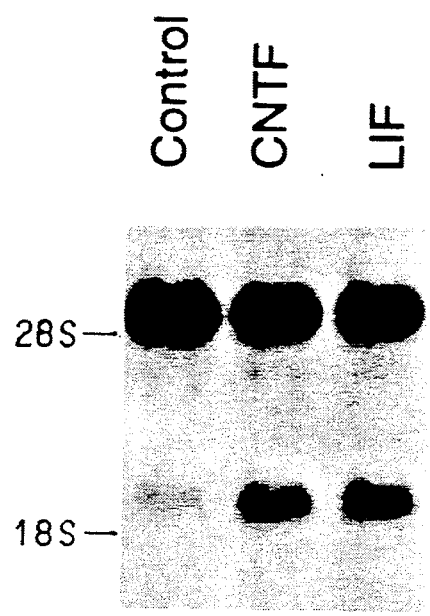
Figure 20B:
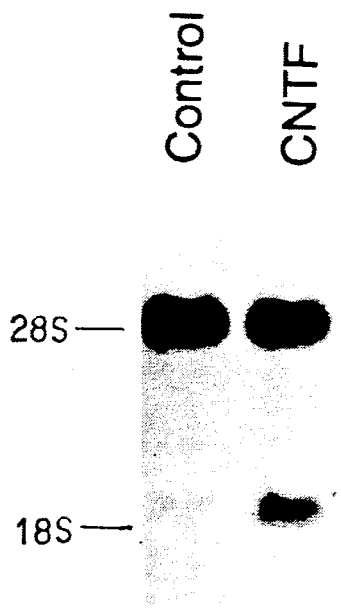

FIGS. 20A–20B. Induction of tis11 by CNTF and LIF in ES cells. ES cells were plated and maintained in an indifferentiated state in the presence of either CNTF (20ng/ml) or LIF (20ng/ml). Total cellular RNA was prepared, electrophoresed on a formaldehyde agarose gel, transferred to nylon membrane and hybridized to $^{32}$p-labelled tis11 probe. In ES cells, CNTF and LIF both produced similar inductions in tis11 gene expression.

Figures 21A, 21B:
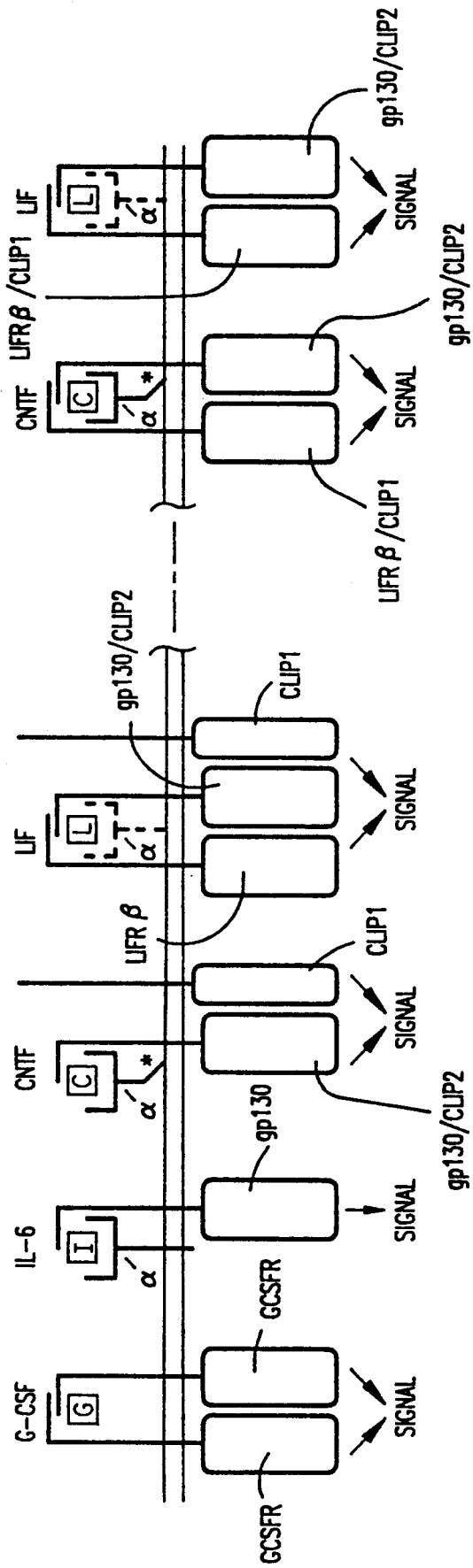

FIGS. 21A–21B. Schematic models of G-CSF, IL-6, CNTF and LIF receptor complexes. A. Model depicting known components of indicated cytokine receptor complexes. B. Revised "unified" models of CNTF and LIF receptor complexes assuming that CLIP1 is LIFR$\beta$. In the model presented in part B, CNTFR$\alpha$ is all that is required to convert a functional LIF receptor complex into a functional CNTF receptor complex. Factors represented as squares; $\alpha$ subunits are known to exist for the IL-6 and CNTF receptor complexes, and are thus depicted with solid lines (asterisk adjacent to CNTFR$\alpha$/membrane junction indicates GPI-linkage), while potential LIFR$\alpha$ component is indicated by a dashed line. Although depicted as membrane bound, $\alpha$ subunits may also function as soluble cofactors.

5. DETAILED DESCRIPTION OF THE INVENTION

The present invention relates to a cell free CNTF/receptor complex and related compounds and their use in promoting the survival, differentiation, proliferation and/or growth of cells which may or may not express CNTFR. For purposes of clarity of disclosure, and not by way of limitation, the detailed description of the invention is divided into the following subsections:

(i) the CNTF/Receptor Complex.
(ii) characteristics of the CNTF/Receptor Complex; and
(iii) uses of the CNTF/Receptor Complex.

The present invention is based on the further discoveries that CNTF and LIF act on neuronal cells via a shared signalling pathways that involves the IL-6 signal transducing receptor component gp130 and that CNTF and LIF require a second, CLIPI/LIFR$\beta$ component to initiate signal transduction. Thus, the detailed description of the invention is further divided into the following subsections:

(iv) CNTF, IL-6 and LIF Share Signal Transducing Components
(v) uses of Shared and Unique Signal Transducing Components.

5.1 The CNTF/Receptor Complex

The present invention relates to the formation of a stable, biologically active cell-free CNTF/receptor complex. It is based, in part, on the production and purification of useful amounts of CNTF and CNTFR and their ability to form a stable, biologically active complex under normal physiological conditions.

For example, useful amounts of CNTF and CNTFR may be prepared by first cloning and sequencing a gene encoding each respective protein. Each cloned gene may then be expressed in a prokaryotic or eukaryotic expression system. Any of a number of protocols available to one skilled in the art may be utilized to clone and sequence CNTF and CNTFR. For example, but not by way of limitation, CNTF may be cloned and sequenced preceding expression in a bacterial expression system, as described in U.S. Pat. application Ser. No. 07/570,651, entitled "Ciliary Neurotrophic Factor," filed Aug. 20, 1990 by Sendtner, et al., International application No. PCT/U.S. 90/05241, which are incorporated in their entirety by reference herein. In addition, CNTFR may, by way of example and not of limitation, be cloned and sequenced, as described in U.S. Patent application No. 07/700,677, entitled "The Ciliary Neurotrophic Factor," filed May 15, 1991 by Davis, et al., and International application No. PCT/U.S. 91/03896 by Davis et al., filed Jun. 3, 1991. In preferred embodiments, CNTF having a sequence substantially as set forth in FIGS. 1A-1B and CNTFR having a sequence substantially as set forth in FIGS. 2A-2D may be used.

The recombinant CNTFR gene may be expressed and purified utilizing any number of methods. In a preferred, nonlimiting embodiment of the invention, CNTFR may be prepared from bacterial cells that express recombinant CNTFR as follows. The gene encoding human CNTFR may be subcloned into a bacterial expression vector, such as for example, but not by way of limitation, pCP110. The resulting plasmid, pRPN151, encodes a recombinant, mature form of human CNTFR (huCNTFR), consisting of 327 amino acids of the mature huCNTFR coding region and three additional amino acids, Met Ser Thr, at the $NH_2$ terminus. Additional manipulations at the beginning of the coding region, as described in Example Section 6, further optimize huCNTFR expression without modifying the protein sequence. This recombinant plasmid may then be transformed into a suitable strain of bacteria, such as *E. coli* strain RFJ26 and grown under culture conditions known in the art to induce synthesis of recombinant protein, so as to obtain useful amounts of recombinant huCNTFR.

The recombinant huCNTFR may be purified by any technique which allows for the subsequent formation of a stable, biologically active CNTF/receptor complex. For example, and not by way of limitation, huCNTFR may be recovered from RFJ26/pRPN151 cells as inclusion bodies, followed by quantitative extraction in 8M guanadinium chloride and dialysis as in Section 7, infra. In order to further purify CNTFR, it may be undesirable to use methods such as conventional ion exchange chromatography, hydrophobic interaction chromatography, or reverse phase chromatography as active CNTFR may be difficult to isolate following these procedures. Rather, the present invention provides for a method of further purifying CNTFR comprising gel filtration. According to the present invention, proteins other than CNTFR that are expressed at low levels (e.g. <2%) may also be purified by this method.

The CNTF/receptor complex may be formed subsequent to the purification of CNTF and CNTFR. Any ratios of CNTF and CNTFR which produce a stable CNTF/receptor complex may be used, including but not limited to, 1:1, 2:1, 3:1, etc. For example, but not by way of limitation, equimolar amounts (e.g., 80 nM) of recombinant CNTF and recombinant CNTFR may be mixed in a physiological buffer solution (e.g., 100 mM Tris HcI, 50 mM NaCl, pH 8.0) at room temperature. The mixture may then be applied to a gel filtration column and the peak corresponding to the CNTF/receptor complex may be recovered for use in numerous assays described infra.

The present invention provides for complexes in which CNTF and CNTFR are covalently or, preferably, non-covalently linked.

The present invention further relates to any complex or molecule which may be used to either promote or, alternatively to antagonize cell differentiation. In particular embodiments of the invention, the CNTF/receptor complex imparting such an effect may be encoded by a hydrid or chimeric nucleic acid sequence. This hybrid or chimeric nucleic acid sequence may be constructed by any of the numerous recombinant DNA methods known in the art such that sequences encoding functional portions of both CNTF and CNTFR are translationally linked; subcloned into either a prokaryotic or eukaryotic expression plasmid such that expression of the hybrid or chimeric nucleic acid sequence is controlled by any of a number of promoter elements compatible with the prokaryotic or eukaryotic host system as well as the orientation of the hybrid gene within the expression plasmid. In a preferred embodiment of the invention, the nucleic acid sequences encoding functional portions of CNTF and CNTFR are subcloned in the same orientation and under control of the same regulatory sequences, resulting in a "dicistronic" construction. The nucleic acid region spanning the fusion junction of the CNTF and CNTFR gene will either possess a sequence promoting splicing of the initial transcript prior to translation or, alternatively, this region will encode a peptide sequence known in the art to promote post-translational proteolytic processing by a protease active in the host cell. The construction of such a hybrid or chimeric molecule promotes the expression of equimolar amounts of both functional components of the CNTF/receptor complex and allows for purification of the CNTF/receptor complex directly from either the prokaryotic or eukaryotic host cell. The present invention also relates to nucleic acid sequences that encode a mutant CNTFR. A given CNTFR gene can be mutated in vitro or in vivo, to create site-specific changes, additions or deletions in the coding region. Any technique for mutagenesis known in the art can be used, including but not limited to, in vitro site directed mutagenesis [Hutchinson, et al.,, J. Biol. Chem. 253:6651 (1978)], use of TAB linkers (Pharmacia), etc. In various nonlimiting embodiments of the invention, hybrid or mutant molecules or complexes prepared as above may possess a number of characteristics that differ from those of the native CNTF/receptor complex. For example, such a hybrid or mutant may be able to promote signal transduction in the absence of CNTF (i.e., without the formation of the CNTF/receptor complex).

As another example, a hybrid or mutant may be capable of binding CNTF without resulting in signal transduction. These CNTFR blocking routants or hybrids may then be assayed for their ability to act as antagonists of signal transduction in the presence of CNTF in any of the assay systems described infra. In preferred embodiments, such CNTFR blocking routants or hybrids may bind CNTF with a higher affinity than that of native CNTFR for CNTF. In yet another embodiment of the invention, a CNTF mutant may be produced that binds to the CNTFR such that the resulting complex is incapable of signal transduction.

P 5.2. Characteristics of the CNTF/Receptor Complex

The present invention relates to a stable CNTF/receptor complex. In a particular embodiment of the invention as described in Section 5.1 and Example Section 6, a biologically active CNTF/receptor complex is formed by adding equimolar amounts of CNTF and CNTFR in a physiological buffer solution at room temperature. The CNTF/receptor complex of this particular embodiment possesses a different mobility in native polyacrylamide gels than either purified fractions of CNTF or CNTFR.

The CNTF/receptor complex may also be characterized according to its biological activity. In CNTF responsive cells, the activity of the CNTF/receptor complex corresponds to that of CNTF.

CNTF promotes cell differentiation as well as the survival of primary neurons. Target cells for CNTF that express CNTFR, include, but are not limited to, cells of the ciliary ganglion, dorsal root ganglion, hippocampus, and motor neurons.

The biological response of CNTF in these target cells is imparted through CNTF/receptor complex participation in a signal transduction pathway (see, for example, Section 9, infra). For example, CNTF mediates growth arrest and differentiation of MAH cell lines. Exposure of a MAH cell line to CNTF rapidly induces a pattern of tyrosine phosphorylation of three distinct CLIP proteins. In addition, phosphorylation of these CLIP genes immediately precedes induction of a characteristic immediate early gene, tis11. These early phosphorylation events in response to CNTF are indicative of the presence of such a signal transduction pathway.

However, in another embodiment of the invention, the CNTF/receptor complex mediates similar effects as described supra on target cells which do not express the CNTF receptor (see, for example, Section 8, infra), provided such cells express a second component referred to herein as a "signal transducing component;" i.e., a second component that interacts with receptor molecules to induce signal transduction, e.g., gp130 associated with the IL 6 receptor system or the beta chain of the receptor for Leukemia Inhibitory Factor (LIF). Cells which express these signal transducing components are said herein to be CNTF/receptor complex responsive. A target cell for the CNTF/receptor complex may be any cell conducive to identification through a signal transduction assay in vitro (e.g., as discussed supra, such as a target cell which demonstrates a phenotypic differentiation, the expression of immediate early genes or the phosphorylation of CLIP proteins) in response to treatment with the CNTF/receptor complex, or a hybrid or mutant thereof that either mimics or alters the normal physiological effect of the CNTF/receptor complex.

The effect of CNTF/receptor complex, or a related hybrid or mutant compound, on target cells can be assayed by any of a number of phenotypic and/or biochemical responses which are characteristic of the specific cell type. If the target cells are responsive to CNTF, the activity of the complex may be measured as a function of CNTF-related biological effects, such as the survival of ciliary ganglion neurons, dorsal root ganglion neurons, or motorneurons, etc.

If the target cells are not responsive to CNTF, but are CNTF/receptor complex responsive, they may be assayed for other markers of differentiation. For example, but not by way of limitation, an M1 cell line may be utilized to test the ability of the CNTF/receptor complex, or a hybrid or mutant protein thereof, to promote differentiation in a manner similar to the IL-6 or LIF-receptor pathway. Undifferentiated M1 cells are round and phase bright and do not adhere to the substrate. Upon differentiation, as promoted through the CNTF/IL-6/LIF receptor family, the M1 cells become more differentiated and adhere to the substrate. Therefore, M1 cultures may easily be scored for this differentiation phenotype.

Cell specific markers may also be utilized, as was described supra for MAH cells, such as an alteration in patterns of CLIP proteins or other patterns of phosphorylation and the activation of immediate early genes (e.g., tis 11;See Section 9, infra).

The ability of the CNTF/receptor complex to promote phenotypic differentiation in M1 cells (e.g., belonging to the IL-6/LIF receptor family) indicates that any other target cell responding to this complex is a target cell for the CNTF/receptor. In addition to myeloid leukemia cells such the M1 cell line, other potential target cells for the CNTF/receptor, or hybrids and routants thereof include leukemia cells, hematopoietic stem cells, megakaryocytes and their progenitors, DA1 cells, osteoclasts, osteoblasts, hepatocytes, adipocytes, kidney epithelial cells, embryonic stem cells, renal mesangial cells, T cells, B cells, etc.

A target cell for the CNTF/receptor complex may be any cell conducive to identification through a signal transduction assay in vitro (e.g., as discussed supra, such as a target cell which demonstrates a phenotypic differentiation, the expression of immediate early genes or the phosphorylation of CLIP proteins) in response to treatment with the CNTF/receptor complex, or a hybrid or mutant thereof that either mimics or alters the normal physiological effect of the CNTF/receptor complex.

5.2.1. Direct $^{125}$I-hCNTF Binding Assay

As discussed supra, another embodiment of the invention relates to the isolation of CNTFR mutants that are altered in their binding capacity for CNTF. In a preferred embodiment of the invention, mutagenesis of pCMX-hCNTFR(12) (assigned accession number NRRL B-18789)is followed by a direct $^{125}$I-hCNTF binding assay as described in U.S. Patent application Ser. No. 07/700,677, entitled "The Ciliary Neurotrophic Factor," filed May 15, 1991 by Davis et al. Briefly, 10 μg hCNTF (560 μg/ml in 10 mM NaPO$_4$, pH7.4) may be iodinated with 1 mCi $^{125}$INa using lactoperoxidase 6 ng/μl (Sigma) for 15 minutes at 20° C. After 15 minutes the reaction may be quenched with an equal volume of buffer containing 0.1 M NaI, 0.1% BSA and 0.1% cytochrome C, 0.3% HOAc, 0.05% phenol red and 0.02% NAN$_3$. Aliquots may be removed for determination of TCA precipitatable counts. The remainder may be loaded onto a BioRad PD-10 Biogel column equilibrated with 0.05 M NaPO$_4$, 0.1 M NaCl, 0.5 mg/ml protamine sulfate and 1 mg/ml BSA. Fractions may be collected and TCA precipitable counts determined. Next, COS cells may be transfected with mutagenized plasmid DNA. After 48 hours, the media may be removed and replaced with 0.25 ml of binding buffer (RPM1 1640 with 10% FBS and 0.1% NAN$_3$) containing $^{125}$I-hCNTF alone or with unlabelled hCNTF. Incubations with $^{125}$I-hCNTF may be for 60 minutes at room temperature. After incubations are complete, the $^{125}$I-hCNTF solution is removed and the cells washed three times with 1.0 ml of binding buffer and then lysed with 0.25 ml of 0.1 N NaOH. This lysate may be transferred to a 12×75 mm polystyrene tube and placed in a gamma counter. Non-specific binding may be determined by the addition of at least 100 fold excess unlabelled hCNTF. After the last wash the plates may be autoradiographed.

CNTFR routants exhibiting either high or little or no CNTF binding may be selected for further analysis. Supernatants from transfected cell lines of interest may be utilized in any number of differentiation assays to determine the ability of each mutant to promote signal transduction.

5.2.2. Signal Transduction Assay

As discussed supra, the M1 cell assay system is useful for measuring the signal transducing ability of members of the CNTF/IL-6/LIF receptor family.

This assay system is also useful to practice further embodiments of the invention, namely to identify mutant CNTF receptors that transduce signals without binding CNTF, and mutant CNTF receptors that bind CNTF but do not induce signal transduction. For example, if a CNTFR mutant gives a weak or non existent signal in the $^{125}$I-hCNTF direct binding assay, then this mutant receptor is scored in the M1 assay for the ability to promote phenotypic differentiation. Conversely, a CNTFR mutant showing increased binding may also be assayed in the M1 system. The mutant CNTF receptor may be mixed with varying amounts of unlabeled CNTF and scored in the M1 assay for the ability to inhibit phenotypic differentiation (e.g, the mutant CNTFR acts as an antagonist to signal transduction pathway).

In a further embodiment of the invention, different target cells of the CNTF/IL-6/LIF family may be identified using the same type of assay as described for M1 cells.

Alternatively, target cells may be identified in an assay system that demonstrates signal transduction, such as phosphorylation of CLIP proteins or immediate early gene induction, as described in Section 9, infra. For example, a culture of putative target cells may be exposed to an effective concentration of CNTF/receptor complex and then evaluated for phosphorylation of CLIP proteins, induction of tis11 immediate early gene expression, etc., in which such evidence of signal transduction indicates that the cells are indeed targets for CNTF/receptor complex.

5.3. Utility of the CNTF/Receptor Complex

According to the present invention, the CNTF/receptor complex, or a hybrid or mutant thereof, may be used to promote differentiation, proliferation or survival in vitro or in vivo of cells that are responsive to the CNTF/receptor complex including cells that express receptors of the CNTF/IL-6/LIF receptor family, or any cells that express the appropriate signal transducing component as evidenced by the characteristics (e.g., phosphorylation of CLIP proteins and/or immediate early gene induction) set forth in section 5.2, supra. Mutants or hybrids may alternatively antagonize cell differentiation or survival.

5.3.1. In Vivo Applications

The present invention may be utilized to identify new target cells for potential therapeutic or diagnostic applications of the CNTF/receptor complex. For example, but not by way of limitation, assays identifying changes in morphology (e.g., progression from rounded to flat cells and the extension of cellular processes and the transition from free-floating to attached cells) or biochemical markers (e.g., the expression of cell specific markers, the activation of cellular genes, such as the immediate early gene, tis 11, or the alteration in phosphorylation patterns, such as the CLIP proteins) or cell growth or proliferation may be utilized to identify such novel target cells.

Conversely, cells responsive to the CNTF/receptor complex may be used to identify CNTF/receptor complex related hybrid or mutant compounds. For example, such cells may be exposed to varying concentrations of CNTF/receptor complex related hybrid or mutant compound, and then the presence or absence and magnitude of physiological effects, such as cell proliferation, cellular morphology, phosphorylation of CLIP proteins, immediate early gene induction, etc. may be determined. If the hybrid or mutant acts as an agonist of CNTF/receptor complex action, physiological changes should be similar to those produced by CNTF/receptor complex. Alternatively, if the hybrid or mutant acts as an antagonist of CNTF/receptor complex action, the physiological changes associated with CNTF/receptor complex action should be diminished or eliminated.

Any such target cell identified as a cell responsive to the CNTF/receptor complex through alterations of morphological or biochemical patterns is a candidate for use in diagnostic assays. Such assays involve testing cells biopsied from patients for sensitivity to a particular treatment protocol involving the CNTF/receptor complex, or a hybrid or mutant thereof which promotes or antagonizes the signal transduction within this family of receptors.

The present invention may be utilized to diagnose diseases and disorders of the nervous system which may be associated with alterations in the pattern of CNTF or CNTFR expression, and hence, formation of the CNTF/receptor complex. For example, an abnormal response to CNTF/receptor complex in cells taken from a patient may support a diagnosis of a neurological disorder in the patient.

Such cell biopsies can be used to detect, prognose, diagnose, or monitor conditions, disorders, or disease states associated with changes in CNTF expression, including in particular, conditions resulting in damage and degeneration of neurons known to respond to CNTF, such as parasympathetic neurons, cholinergic neurons, spinal cord neurons, neuroblastoma cells and cells of the adrenal medulla. such diseases and conditions include but are not limited to central nervous system trauma, infarction, infection, degenerative nerve disease, malignancy, or post-operative changes including but not limited to Alzheimer's Disease, Parkinson's Disease, Huntington's Chorea, and amyotrophic lateral sclerosis.

In a further embodiment, the present invention has utility regarding any target cell identified through a bioassay system as described supra. Any such target cell is a candidate for use in an in vitro system to detect, prognose, diagnose, or monitor the condition of the differentiation disorder or disease including, but not limited to malignant or neoplastic conditions, and in particular diseases or disorders involving the following cells: leukemia cells, hematopoietic stem cells, megakaryocytes and their progenitors, DA1 cells, osteoclasts, osteoblasts, hepatocytes, adipocytes, kidney epithelial cells, embryonic stem cells, renal mesangial cells, T cells, B cells, etc.

5.3.2. In Vivo Applications

The present invention may be used to treat disorders of any cell responsive to the CNTF/receptor complex, including cells that are responsive to CNTF, as well as cells that are not. In preferred embodiments of the invention, disorders of cells that express members of the CNTF/IL-6/LIF family may be treated according to these methods. Examples of such disorders include but are not limited to those involving the following cells: leukemia cells, hematopoietic stem cells, megakaryocytes and their progenitors, DA1 cells, osteoclasts, osteoblasts, hepatocytes, adipocytes, kidney epithelial cells, embryonic stem cells, renal mesangial cells, T cells, B cells, etc.

Accordingly, the present invention provides* for methods in which a patient suffering from a CNTF-related neurological or differentiation disorder or disease is treated with an effective amount of the CNTF/receptor complex, or a hybrid or mutant thereof. The CNTF/receptor complex or appropriate hybrids or routants thereof, may be utilized to treat disorders or diseases as described for CNTF in International application PCT/U.S. 90/05241 by Sendtner, et al. and for CNTFR in U.S. Patent application Ser. No. 07/700,677, entitled "The Ciliary Neurological Receptor," filed May 15, 1991 by Davis et al. Therapeutic methods comprising administering the CNTF/receptor complex, a CNTFR mutant inducing signal transduction without binding CNTF or a CNTF/receptor complex antagonist (e.g.,, a CNTFR mutant with a high CNTF binding affinity that does not induce signal transduction), are within the scope of the invention.

The present invention also provides for pharmaceutical compositions comprising the CNTF/receptor complex, hybrid or mutant thereof in a suitable pharmacologic carrier.

The CNTF/receptor complex, hybrid or mutant thereof may be administered systemically or locally. Any appropriate mode of administration known in the art may be used, including, but not limited to, intravenous, intrathecal, intraarterial, intranasal, oral, subcutaneous, intraperitoneal, or by local injection or surgical implant. Sustained release formulations are also provided for.

5.3.2.1. Formation of the Active Ingredient

The active ingredient, which may comprise the stable CNTF/receptor complex, or a hybrid or mutant thereof, should be formulated in a suitable pharmaceutical carrier for administration in vivo by any appropriate route including, but not limited to injection (e.g., intravenous, intraperitoneal, intramuscular, subcutaneous, endoneural, perineural, intraspinal, intraventricular, intrathecal etc.), by absorption through epithelial or mucocutaneous linings (e.g., oral mucosa, rectal and intestinal mucosa, etc.); or by a sustained release implant, including a cellular or tissue implant.

Depending upon the mode of administration, the active ingredient may be formulated in a liquid carrier such as saline, incorporated into liposomes, microcapsules, polymer or wax-based and controlled release preparations, or formulated into tablet, pill or capsule forms.

The concentration of the active ingredient used in the formulation will depend upon the effective dose required and the mode of administration used. The dose used should be sufficient to achieve circulating plasma concentrations of active ingredient that are efficacious. For example, when CNTF/receptor complex is the active ingredient, a circulating serum concentration level ranging from about 50 picomolar to 100 nanomolar may be used. Effective doses may be extrapolated from dose-response curves derived from in vitro or animal model test systems.

In an alternative embodiment CNTF/receptor complex preparations are provided, in which more than one CNTF/receptor complex are linked together either directly or through another member, such as a bead.

5.4 CNTF, IL-6 AND LIF SHARE SIGNAL TRANSDUCING COMPONENTS

Signal transduction pathways activated by both CNTF and LIF in the MAH cell line, as well as in other neuronal cell lines, were compared to those activated by LIF and IL-6 in hemopoietic cell lines. In U.S. Patent application Ser. No. 676,847 filed Mar. 28, 1991, which is incorporated by reference herein, we described the possible interaction between CNTF, the CNTF receptor and the signal transducer gp130. The studies described herein confirmed the finding that the CNTF signalling pathway involves gp130 and further revealed that LIF also utilizes a signalling pathway that involves the IL-6 signal transducer, gp130. Also described herein is the discovery that CNTF and LIF share a second gp130-like receptor component. This suggests that CNTFR (CNTFR$\alpha$)is all that is required to change the LIF receptor complex into a functional CNTF-responsive receptor complex.

In the case of IL-6, a complex between IL-6 and its receptor component binds gp130, which then somehow activates the signal transduction process [Taga et al., Cell 58:573-581 (1989); Hibi et al., Cell 63:1149-1157 (1990)]. The ability of gp130 to transduce functional signals correlates with its ability to be phosphorylated on tyrosine [Murakami et al., Proc. Natl. Acad. Sci. USA 88:11349-11353 (1991)]. Here we have identified cell lines that allow for comparison of responses to CNTF and LIF, distant relatives of IL-6. Strikingly, the CNTF responsive neuronal cell lines examined displayed indistinguishable phenotypic and biochemical responses to LIF; in contrast, LIF responsive hemopoietic cells did not respond to CNTF. CNTF and LIF responses in neuronal cells appear to initiate with the tyrosine phosphorylation of the three CLIPs, at least two of which (CLIP1 and CLIP2) are cell surface proteins that can interact to form a stable, immunoprecipitable complex.

The CLIP phosphorylations precede and, based on kinase inhibitor studies, are apparently required for subsequent characteristic gene inductions. LIF and CNTF display parallel dose responses, time courses and inhibitor profiles with respect to these phosphorylations and gene inductions, and prior treatment with either factor will down-regulate responses to the other. Not only are the CNTF and LIF induced signalling events essentially indistinguishable in neuronal cells, but they appear identical to those induced by LIF in hemopoietic cells. These events are also very similar to those induced by IL-6 in hemopoietic cells, except that CLIP1 phosphorylation is specifically characteristic of CNTF and LIF responses. We provide a basis for the similarities in the CNTF, LIF and IL-6 signalling pathways by presenting evidence that one of the CLIPs (CLIP2)is the IL-6 signal transducer gp130.

Our findings raise many questions concerning the interactions of the various CNTF and LIF receptor components with gp130/CLIP2. CNTF can bind directly to the IL6R-related CNTFR [Davis et al., Science 253:59-63 (1991)] that, based on our data and by analogy to the IL-6 system (FIG. 21A), then presumably interacts with gp130. However, the CNTF receptor complex apparently also includes another cell surface protein, CLIP1, that is tyrosine phosphorylated in response to CNTF and can directly interact with gp130 (FIG. 21A). LIF is known to bind a recently cloned gp130-related receptor component with a molecular weight of approximately 190 kD (hereon LIFR), and the existence of a LIF-receptor β (hereon LIFR) has also been proposed [Gearing et al, Cell 66:9-10 (1991)]. Our data indicates that the LIF receptor complex also includes CLIP1 and gp130 (FIG. 21A). Finally, the receptor complex for IL-6/CNTF/LIF-related G-CSF is apparently a homodimer of the gp130-related G-CSF receptor [Fukunaga et al, EMBO J. 10:2855-2865 (1991)] (FIG. 21A).

Although the receptor complexes portrayed in FIG. 21A mediate binding to structurally related ligands, as depicted they are unsatisfyingly different. It is possible to propose more "uniform" receptor models, however, if one considers the possibility that CLIP1, which is similar in size to LIFRβ, is indeed LIFRβ (FIG. 21B). Thus, the CNTF and LIF receptor complexes would each utilize two different gp1301-like components, LIFRβ/CLIP1 as well as gp130 itself. These two β components would directly interact based on our co-precipitation data, and they would both be inducibly phosphorylated on tyrosine. Supporting such a receptor structure, recent crosslinking data [Godard et al., J. Biol. Chem. 267,( in press)]reveal that LIF can be bound to two distinct proteins with sizes that would correspond to those of LIFRβ/CLIP1 and gp130. The involvement of two β components in the LIF and CNTF receptor complexes would be reminiscent of the G-CSF receptor structure (FIG. 21B) ad raises the possibility that the IL-6 receptor complex may also involve a homodimer of gp130. In fact, it may be that β-subunit dimerization and/or activation leads to activation of the signalling process, as proposed for receptor tyrosine kinases and some cytokine receptors [Aaronson et al., Science 254:1146-1153 (1991); De Vos et al., Science 255:306-312 (1992)].

In the model presented in FIG. 21B, the β receptor components would act to modulate the binding of the factors to the components, and thus be responsible for conferring ligand specificity upon the shared transducing machinery. Cross-linking data [Godard et al., J. Biol. Chem. 267 (in press)] might suggest that for LIF, as with G-CSF, such components may not be required. Thus, the CNTFR component would be all that is required to convert a functional LIF receptor into a functional CNTF receptor. The latter possibility, together with the restricted expression of CNTFR to the nervous system, adrenal gland, sciatic nerve and skeletal muscle [Davis et al., Science 253: 59-63 (1991)], could explain why all CNTF-responsive neuronal cells also respond identically to LIF [see above; also Rao et al., Dev. Biol. 139: 65-74 (1990)], whereas LIF responsive cells outside of the nervous system do not respond to CNTF.

Interestingly, the components for IL-6 or CNTF do not have to be membrane bound in order to interact with their transducing components [Taga et al., Cell 58:573-581 (1989)]. Thus, complexes containing these factors together with soluble forms of their receptors may act as heterodimeric factors for cells that are not capable of responding to the factor alone (because they do not express the appropriate receptor), but which do express the appropriate transducing components. The possibility that such heterodimeric complexes actually operate as soluble factors in vivo is supported by the hornology between the receptor components and one of the two subunits of natural killer cell stimulatory factor, a normally occurring heterodimeric factor [Gearing and Cosman, Cell 66:9-10 (1991)]. Furthermore, the unusual and readily cleavable glycosyl-phosphatidylinositol linkage of the CNTFR to the cell surface points toward a role for regulated release of this receptor component [Davis et al., Science 253:59-63 (1991)].

While the receptor models presented above need further experimental verification, they clearly have relevant precedents. A plethora of G-protein coupled receptors similarly interact with a small number of signal transducing heterotrimeric G-proteins, allowing a vast array of different signals (e.g. neurotransmitters, polypeptide hormones and odorants) to converge on a relatively modest number of signalling pathways [Gilman, Ann. Rev. Blochem. 56:615-647 (1987)]. More directly relevant to the gp130-coupled receptor systems are those of IL-3, IL-5 and GM-CSF. The overlapping activities and similar tyrosine phosphorylations induced by IL-3, IL-5 and GM-CSF led to the finding that these factors use distinct receptor components but share components (reviewed in Nicola and Metcalf, Cell 67: 1-4 (1991); Miyajima et al. Annu. Rev. Immunol (1992) (in press). Once again, the receptor components are primarily involved in binding the factors, but lack extensive cytoplasmic domains and thus do not appear to have signal transducing capabilities. The shared subunits appear to be required for high affinity binding, and are responsible for initiating signal transduction events that involve tyrosine phosphorylations. As with gp130 (and presumably LIFR/CLIP1), the subunits are themselves tyrosine phosphorylated, but do not appear to have inherent kinase activity. Although little is known about the mechanisms by which these subunits are tyrosine phosphorylated, the multi-component IL2 receptor also utilizes a subunit (IL2R) that is responsible for high affinity binding and signal transduction, and this chain is tyrosine phosphorylated by a src-like tyrosine kinase (Ick) with which it physically associates (reviewed in Miyajima et al., in press). Interestingly, CLIP phosphorylation and IL-2 induced Ick phosphorylation display similar susceptibility profiles to kinase inhibitors [Hatakeyama et al., Science 252:1523-1528 (1991)]. That is, both phosphorylations are susceptible to staurosporine but not to H-7, suggesting that similar tyrosine kinases may be involved; CLIP3 may be a candidate for such a src-related kinase.

In several important ways, CNTF appears to be quite unusual compared to its distant cytokine relatives. Most importantly, CNTF has a very restricted receptor component distribution and, thus far, it is primarily cells of the nervous system that appear responsive to CNTF [Davis et al., Science 253: 59-63 (1991)]. This restriction contrasts with the broad actions of the cytokines related to CNTF; the CNTF example suggests that additional related cytokines displaying a very restricted range of actions may exist. Identification of the MAH cell line provides a neuronal precursor cell line which displays physiologically relevant responses to CNTF and LIF as well as to factors using unrelated receptor systems, such as FGF and NGF. Use of the MAH cell line should contribute to the understanding of how different factors, utilizing distinct signalling pathways, can interact to effect the growth and differentiation of neuronal progenitor cells. Contrasting the responses of MAH cells and hemopoietic cell lines to the cytokines should also provide insight into the mechanisms by which distinct cellular contexts alter the perception and interpretation of a very similar initial signal.

5.5 Uses of Common and Unique Receptor Components

As described herein, CNTF and LIF share components of a receptor complex/signal transduction pathway. Accordingly, CNTF alone, or in combination with CNTFR(CNTFα), may prove to be useful as a means of initiating a response in a cell normally responsive to LIF. Depending on the receptor components a cell has, it may respond to CNTF or to a combination of CNTF and CNTFR. If a cell has gp130, LIFRIβ and CNTFα (as appears to be the case with ES cells), CNTF alone will have the same effect at LIF. If the cell has only gp130 and LIFRβ, CNTF and CNTFR in combination would mimic the effect of LIF.

5.5.1 Use of CNTF to Prevent the Differentiation of Embryonic Stem Cells

We have recently determined that CNTF can be utilized in place of LIF to prevent the differentiation of ES cell. Embryonic stem (ES) cells, totipotent cells isolated from pre-implantation-stage mouse embryos, can be cultured and manipulated in vitro and then reincorporated into a host embryo where they can develop normally and contribute to all cell lineages including the germ line. ES cells, thereby, provide an ideal vector system for the introduction of a specific mutation into mice.

Maintenance of the totipotent ES cells in culture requires either the presence of a feeder layer of fibroblasts (e.g., STO cells) or the soluble factor leukemic inhibitory factor (LIF) Smith, et al. Nature 336, 688-690 (1988); Williams, et al. Nature 3365, 684-687 (1988). The use of feeder cells is very reliable, but the preparation of the feeder layers is time-consuming. STO cells must be treated for 2-3 hrs. with mitomycin C to arrest their growth, then after several washes with PBS the STO cells can be plated onto gelatin-coated plates. The plates can be used the following day, but are only good for 1 week after plating (Robertson, Nature-323, 445-448 (1987). To circumvent the problem of feeder layers, Williams et al., Nature (1988) supra, and Pease and Williams, Exp. Cell Res. 190, 209-211., (1990) found that ES cells maintained in the absence of feeder cells retained their potential to form germ-line chimeras, provided LIF was included in the culture media.

ES cells cultured in the presence of CNTF, but in the absence of feeder cells and LIF, will retain the characteristic stem-cell morphology of compact colonies of small cells. This is the first example of a factor other than LIF which will prevent the differentiation of ES cells. The existence of two factors which elicit a similar response, provide further opportunity to study the regulatory mechanisms by which ES cells are diverted from differentiation.

5.5.2 Activation of LIF Responsive Cells Using CNTF/CNTFR

As described herein, the combination of CNTF and CNTFR or soluble CNTFR (sCNTFR) should bind to and activate any cell that responds to LIF. LIF responsive cells are, however, fairly ubiquitous, thus the use of CNTF and its soluble receptor to activate such cells would not be expected to provide any forseeable advantages as far as enhanced specificity. In addition, the efficiency of the soluble receptor/CNTF complex appears to be much lower than if the CNTFR is attached to the cell surface by the GPI anchor.

To increase both the specificity of the CNTF/CNTFR complex as well as its efficiency, the present invention contemplates the targeting of cells by complexing the CNTFR to the surface of a target cell and subsequently using CNTF to activate such a cell. In an alternative embodiment, the CNTF/CNTFR complex is modified in such a way as to make it specific for a particular target cell.

Methods of targeting proteins, such as CNTFR, to cell surfaces are known to those skilled in the art. In general, such proteins are attached to cell surfaces using a linking molecule, a molecule that is capable of binding to both the CNTFR as well as the target cell. Preferably, such a linking molecule would allow flexible binding to a naturally occurring receptor on a target cell. For example, attachment of a linking molecule with a terminal galactose to CNTFR would allow for attachment of such a complex to asialoglycoprotein receptors in the liver. Another example might include attachment of an Fc containing linking molecule to CNTFR that would allow attachment of CNTFR to target cells containing Fc receptors.

Alternatively, antibodies, preferably monoclonal antibodies, would be effective as linking molecules. For example, antibodies that recognize a particular cell surface receptor could be linked to the CNTFR. Alternatively, an epitope could be attached to CNTFR, wherein such an epitope is recognized by a linking antibody that binds both the CTNFR-epitope complex and an epitope on a target cell. If an antibody directed against a target cell binds to an unknown epitope, it could be identified by panning random peptide expression libraries [see, for example PNAS 89:1865 (1992)].

If CNTFR is attached to the surface of a target cell, the cell can then be activated by the addition of CNTF. Alternatively, CNTFR attached to a linking molecule (a molecule capable of attaching it to the surface of a target cell) can be combined with CNTF. In such a case, the active agent would be the CNTF/CNTFR/linking molecule complex.

5.5.3 Identification of CNTFR Antagonists

Based on the identification herein of signal transduction pathways shared by IL-6, LIF and CNTF, it would follow that the the identification of a soluble CNTFR analog that would bind to CNTF, and interact with LIFRβ and gp130 to form a complex, but not be capable of transducing a signal, would also function as an effective inhibitor of activation by LIF or IL-6. Mutants of CNTF may also display these activities.

In a specific embodiment, HepG2 cells, which respond to LIF and IL6 in the "acute phase response" involving the transcriptional upregulation of a variety of genes including fibrinogen are used to provide an assay system for CNTF agonists or antagonists. It has been demonstrated that reporter constructs consisting of ChAT and the responsive gene's upstream sequences (i.e. the fibrinogen promoter) will accurately report functional signalling by IL-6 by upregulating ChAT activity. A reported construct linked to a secreted or cell surface enzyme (such as alkaline phosphatase) could be used to screen routants of CNTF-sCNTFR for the ability to block LIF or IL6 activaton of the reporter. The routants could be transfected into the HepG-2 cells and screened in 96 well plates.

Alternatively, HepG-2 cells transfected with CNTFR would provide a valuable assay system for screening for CNTF activators and/or inhibitors.

6. EXAMPLE: PRODUCTION OF HUMAN CNTF RECEPTOR IN *E. COLI*

1. Materials and Methods

1. Construction of pCP110

The parental plasmid expression vector, pCP110, is described in Masiakowski, et al., J. Neurochem. 57:1003–1012 (1991).

2. CONSTRUCTION OF A VECTOR FOR EXPRESSION OF huCNTFR 1

Plasmid pRPN151 was generated by replacing the DNA between the unique SaiI and EagI restriction sites in pCP110 with a PCR fragment copied from plasmid pCMX-hCNTFR(12) with the use of the DNA primers shown in FIG. 3. Human CNTFR1 consists of the 327 amino acids of the mature huCNTFR sequence and three additional amino acids of the sequence Met-Ser-Thr at the $NH_2$-terminus. The three additional amino acids were included in order to signal translation initiation at the desired amino acid position and in order to simplify subsequent genetic engineering manipulations. At the same time, the DNA sequence was further modified at the beginning of the coding region in order to optimize expression without modification of the protein sequence. This was accomplished by incorporating the desired changes into the sense PCR primer (FIG. 3). Plasmid pRPN151 was then transfected into the *E. coli* strain, RFJ26. Under appropriate induction conditions of RFJ26/pRPN151 cells, huCNTFR1 reached levels representing 10–20% of total protein.

3. PURIFICATION OF huCNTFR1

The majority of the receptor synthesized in RFJ26/pRPN151 cells was localized in inclusion bodies from which it was quantitatively extracted in 8 M guanidinium chloride and recovered in soluble form by dialysis, as described for recombinant rat and human CNTF (International application No. PCT/U.S. 90/05241, filed Sep. 14, 1990 by Sendtner et al.). The recovery of active, correctly folded receptor was accomplished by gel filtration such that correctly folded CNTFR1 molecules would elute at their true size, away from the aggregated protein in the void volume.

6.2. Results

Analysis by absorbance at 280 nm and electrophoresis on reducing SDS-PAGE gels of the proteins eluting from such a column revealed that even though most of the receptor eluted in the void volume (30–40% pure) apparently in aggregate form, some receptor eluted in a distinct, sharp peak (80–90% pure), at the proper molecular weight position (40 kD). The receptor in the latter peak represented 10–50% of the receptor in the starting material, depending on the refolding conditions (FIGS. 5A–5B).

Analysis of the elution profile on native gels showed that the receptor protein in the void peak did not enter the gel, as would be expected for aggregated protein, whereas receptor in the 40 kD peak migrated as a sharp band, as would be expected for a population of molecules having a common conformation.

7. EXAMPLE: FORMATION OF THE CNTF/RECEPTOR COMPLEX

The 40kD peak recovered as described in Section 6.1.3. was utilized in a mixing experiment with purified rat CNTF.

7.1. Materials and Methods

A constant amount of receptor with increasing amounts of rat CNTF were mixed and the samples run on a pH 7.4 native gel system as described by Goldenberg [Analysis of Protein Conformation by Gel Electrophoresis, in: "Protein Structure", ed: Creighton; IRL Press, Oxford (1989)].

Additionally, purified receptor and rat CNTF were mixed in a physiological buffer solution (100 mM Tris-HCl, 50ram NaCl, pH 8.0) at room temperature and loaded on a Superdex-75 column (Pharmacia). An absorbance peak corresponding to the receptor-CNTF complex was recovered and stored at 5° C. for 48 hours, at which time a portion of the sample was again subjected to gel filtration as described supra.

7.2 Results

When receptor from the void peak was mixed with rat CNTF and analyzed on native gels, the receptor remained in the well, along with some of the CNTF. In contrast, when receptor from the 40 kD peak was mixed with rat CNTF, the two proteins migrated as a single band in a new position of the gel (FIG. 6). The shift in gel mobility appears complete at approximately equimolar concentrations of CNTF and CNTF receptor. These results indicate that huCNTFR1 associates tightly with CNTF.

At that time, analysis of a portion of the sample on the same gel filtration column described above indicates that all the protein eluting in a major absorbance peak corresponds to the receptor-CNTF complex, with no evidence of peaks corresponding to the individual protein components. As a control, a second portion of the sample was analyzed by reverse phase chromatography using a C8 cartridge (Applied Biosystems)in 0.1% trifluoroacetic acid-acetonitrile. acetonitrile. As expected, and previously observed with other receptors [Cunningham, et al.,, Science, 254, 821–825 (1991)] in this strong acid-organic solvent mixture the receptor-CNTF complex dissociates to its two individual components, confirming its composition.

These results indicated that under the conditions of these experiments, i.e., at a receptor and CNTF concentration of 80 nM and nearly physiological ionic strength, pH and temperature conditions, recombinant CNTF receptor forms a stable complex with CNTF.

8. EXAMPLE: THE CNTF/RECEPTOR COMPLEX PROMOTES DIFFERENTIATION OF MYELOID LEUKEMIA CELLS

8.1. Materials and Method

8.1.1. Cell Culture Conditions

M1 cells, a myeloid leukemia-derived cell line, were cultured in Dulbecco's Modified Eagle's Medium and 10% horse serum. They were seeded at a density of 50,000 cells per well in NUNC 24 well plates. Oytokines and/or CNTF receptor were added to each well and cultures were scored for differentiated phenotype 5 days later. Soluble CNTF receptor was produced in *E. coli* and purified to homogeneity.

8.1.2 Scoring by Phenotype

Undifferentiated M1 cells are round and phase bright and do not adhere to the substrate. These are scored (−). As the cells become more differentiated, they adhere to the substrate, become less phase bright, assume irregular to spindle shaped morphology, and extend processes. Cultures are scored (+)to (+ + + +) depending on the extent to which they have these features. Under optimal conditions, IL-6 treatment gives a score of (+ +) and LIF gives a score of (+ + +). Extremely high concentrations of CNTF and CNTFR gives the strongest expression of these characteristics and were scored (+ + + +).

8.2. Results

At concentrations of 20 ng/ml, maximal responses of the cells was observed to IL-6 (+ +) and to LIF (+ + +). Table 1 shows the response of M1 cells treated with varying combinations of rat CNTF and soluble human receptor. Table 2 shows the response of the cells to varying combinations of human CNTF with human receptor. Clearly, the combination of CNTF with its receptor is much more effective than either one alone in eliciting a response. The receptor alone did not cause differentiation at any concentration tested, although at very high concentrations, CNTF alone did seem to cause a response. Finally, for some experiments the native receptor was produced in COS cells and cleaved from the cell surface by treatment with phospholipase C. In these experiments, the concentrations of soluble receptor was not determined. The combination of this receptor with 200 ng/ml rat CNTF also caused differentiation, whereas neither CNTF nor CNTFR alone had this effect.

TABLE 1

| human CNTFR (ng/ml) | rat CNTF (ng/ml) | | | |
|---|---|---|---|---|
| | 0 | 20 | 100 | 500 |
| 0 | − | − | − | +/− |
| 40 | − | + | + | + |
| 200 | − | + | + + | + + + |
| 1000 | − | + + | + + + | + + + |

TABLE 2

| human CNTFR (ng/ml) | human CNTR (ng/ml) | | | | | | | |
|---|---|---|---|---|---|---|---|---|
| | 0 | 20 | 100 | 500 | 1000 | 5000 | 10000 | 25000 |
| 0 | − | − | − | − | +/− | + | + | + + |
| 40 | − | − | − | +/− | ND | ND | ND | ND |
| 200 | − | − | +/− | + | ND | ND | ND | ND |
| 1000 | − | − | + | + + | + + + | + + + | + + + | + + + + |

9. EXAMPLE: CNTF RESEMBLES LIF IN MEDIATING PHOSPHORYLATION OF CLIP PROTEINS AND EXPRESSION OF IMMEDIATE EARLY GENES

9.1. Materials and Methods

9.1.1. Reagents

Preparation and purification of recombinant rat CNTF used in this study have been previously described [Masiakowski et. al., J. Neurochem. 57:1003–1012 (1991)]. Murine IL-6 (mIL-6) was purchased from UBI (Upstate Biotech., Inc. N.Y.), while recombinant human LIF was from Amgen Biologicals (Calif.). bFGF purified from bovine brain was purchased from R&D Systems, while NGF was purified from mouse submaxillary gland. Protein Kinase inhibitors used include H-7 [1-(5-1soquinolinesulfonyl)-2-methylpiperaine dihydrochloride, Seikagaku Kogyo Co.) and staurosporine (Kamiya Biotaed. Co.). Antiphosphotyrosine monoclonal antibodies conjugated to agarose beads was from Upstate Biotech., Inc. (N.Y.).

9.1.2. Cell Structure

MAH cells were maintained in culture as previously described [Birren et. al., Neuron 4:189–201 (1990)]. Briefly, cells were plated onto dishes precoated with poly-D-lysine (100 ug/ml) and laminin (10 ug/ml), at a density of 6 K/6 mm well, or 40 K/16 mm well. Medium used was modified L15-$CO_2$ medium supplemented with 10% FBS and dexamethasone (5 uM). IARC-EW-1 (Ewing sarcoma cells) and SK-N-LO (neuroepithelioma cells) was cultured in RPMI medium with 10% fetal bovine serum supplemented with 2 mM L-glutamine and 100 units/ml penicillin and streptomycin. PC12 cells were cultured in Dulbecco's modified Eagle's medium supplemented with 6% horse serum, 6% calf serum, 2 mM L-glutamine and 100units/ml penicillin and streptomycin.

9.1.3. MTT Assay, $^3$H-Thymidine Incorporation Assay and ChAT Assay

MAH cells were treated with factors for various periods of time, prior to the addition of MTT dye (final concentration of 0.5 mg/ml). Incubation was continued for 8 hrs, and DMSO was added to solubilize the dye product taken up by vital cells. The optical density at 570–650nm was quantitated using the Flow Titretek multiscan apparatus. For $^3$H-thymidine incorporation assay, cells were treated with various factors for different periods of time, and $^3$H-thymidine (NEN-NET-027E) was added at a final concentration of 1 uCi/ml and incubated for 4 hrs at 37° C. Cells were then washed three times with PBS, lysed with NaOH (0.5 N) for 2 hrs at room temperature and 3H-DNA was counted. ChAT were performed using standard techniques. Briefly, cells were treated with various factors, washed with ice cold PBS, ChAT harvest buffer containing 20 mM Tris-HCl (pH 8.6) and 0.1% Triton X-100 was added and incubated for 15 min. on ice. Cell extracts were then incubated for 60 min. at 37° C. with a reaction mixture containing 11 mM choline chloride, 0.2 mM 14C-acetyl CoA, 0.14 mM physostigmine, 300 mM NaCl. 50 mM $Na_2PO_4$, 20mM EDTA. An aliquot of this mixture was mixed with scintillation fluid containing acetonitrile/teraphenylboron (5 mg/ml), and counted.

9.1.4. RNA Isolation and Analysis

Cells were plated at a density of $5 \times 10^6$ cells on 100 mm dishes, and treated with factors for various periods of time. Total RNA was prepared by guanidinium thiocyanate method as described previously [Chomczynski et al., Anal. Biochem. 162:156-159 (1987)]. Ten ug RNA was electrophoresed on a formaldehyde agarose gel, transferred to a nylon membrane (MSI), and hybridized to 32p-probes labelled by random oligo-priming (Stragene). The probes used included tis11 (2.3 kb EcoRIfragment), c-fos (1kb Pst fragment), rat CNTF receptor (rCNTFR, 0.4 kb Pst fragment), and GAPDH (1.25 kb Pst fragment).

9.1.5. Protein Isolation, Immunoprecipitation and Immunoblotting

For the detection of protein tyrosine phosphorylation, approximately $1-2 \times 10^6$ cells were starved for 60 min. in serum-free, defined medium, treated with various factors for 5 min., and protein lysates prepared with RIPA buffer (supplemented with proteinase and phosphatase inhibitors) as previously described [Glass et al., Cell 66:405-413 (1991)]. To prepare total protein samples, protein loading dye was added directly to the RIPA lysate supernatants and boiled for 3 min. at 90° C. Alternatively, supernatants from the RIPA lysates were precipitated overnight at 4° C. with 100ul of agarose conjugated anti-phosphotyrosine antibodies (4G10), washed $3 \times$ with the RIPA buffer. Proteins were eluted from the agarose beads wit 200ul of $1 \times$ protein loading dye and boiled for 3 min. Fifty microliter of either the total protein samples or the imunoprecipitate was electrophoresed on 10% SDS-polyacrylamide gels, immunoblotted with anti-phosphotyrosine antibodies as previously described [Glass et al., Cell 66:405-413] and specific proteins detected with 125I-labeled goat anti-mouse polyclonal antibody (1 ul of 4.91 uCi/ug per 1 ml buffer, DuPont). For the immunoprecipitation of ERK proteins in PC12 cells, the cell lysate was immunoprecipitated with an ERK-specific antibody (Zymed, Inc.), followed by a Goat anti-mouse IgG antibody conjugated to agarose. The precipitate was electrophoresed as above and immunoblotted with the same ERK antibody.

9.1.6 Cell Surface Biotinylation Assay

Following a 5 minute incubation with LIF or CNTF to induce CLIP phosphorylation, cells were washed in 5 ml PBS supplemented with 1 mM orthovanadate (PBSV), then incubated for 10 minutes on ice in PBSV containing 1 mg/ml NHS-SS-biotin (3-sulfosuccinimido 3-[2-(biotinamido) ethyl]dithio]proprionate; Pierce), a membrane-impermeant reagent. The plates of cells were then washed with tris-buffered saline containing orthovanadate and lysed with RIPA buffer as described above. Lysates were precipitated with immobilized anti-phosphotyrosine antibody as described, then bound phosphoproteins were removed from the beads by boiling for 5 minutes in 50 mM tris pH 8.2 containing 1% SDS. Biotinylated proteins were precipitated from this solution by incubation for 1 hour with 20L streptavidin-agarose (Pierce). The supernatant containing the non-biotinylated proteins was subjected 5 to SDS PAGE after the addition of sample buffer. The beads containing biotinylated proteins were washed once in the binding buffer, then the bound biotinylated proteins were eluted from the beads by boiling for 5 minutes in $2 \times$ SDS PAGE sample buffer containing 10% $\beta$-mercaptoethanol. Anti-phosphotyrosine immunoblotting on these samples was performed as described above.

9.2.1. CNTF and LIF Mediate Growth Arrest and Differentiation of MAH Cells

Figure 7A:
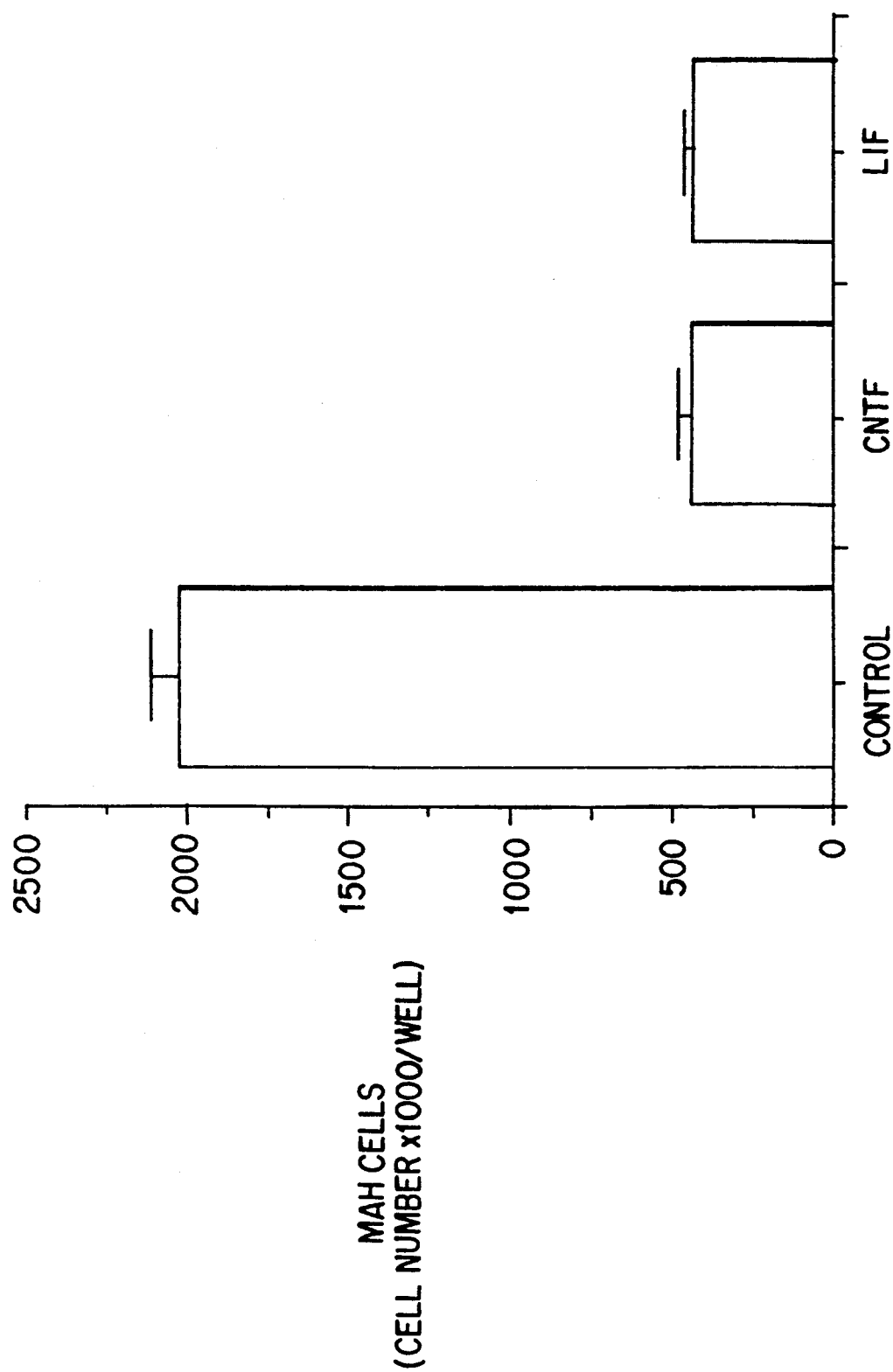
Figure 7B:
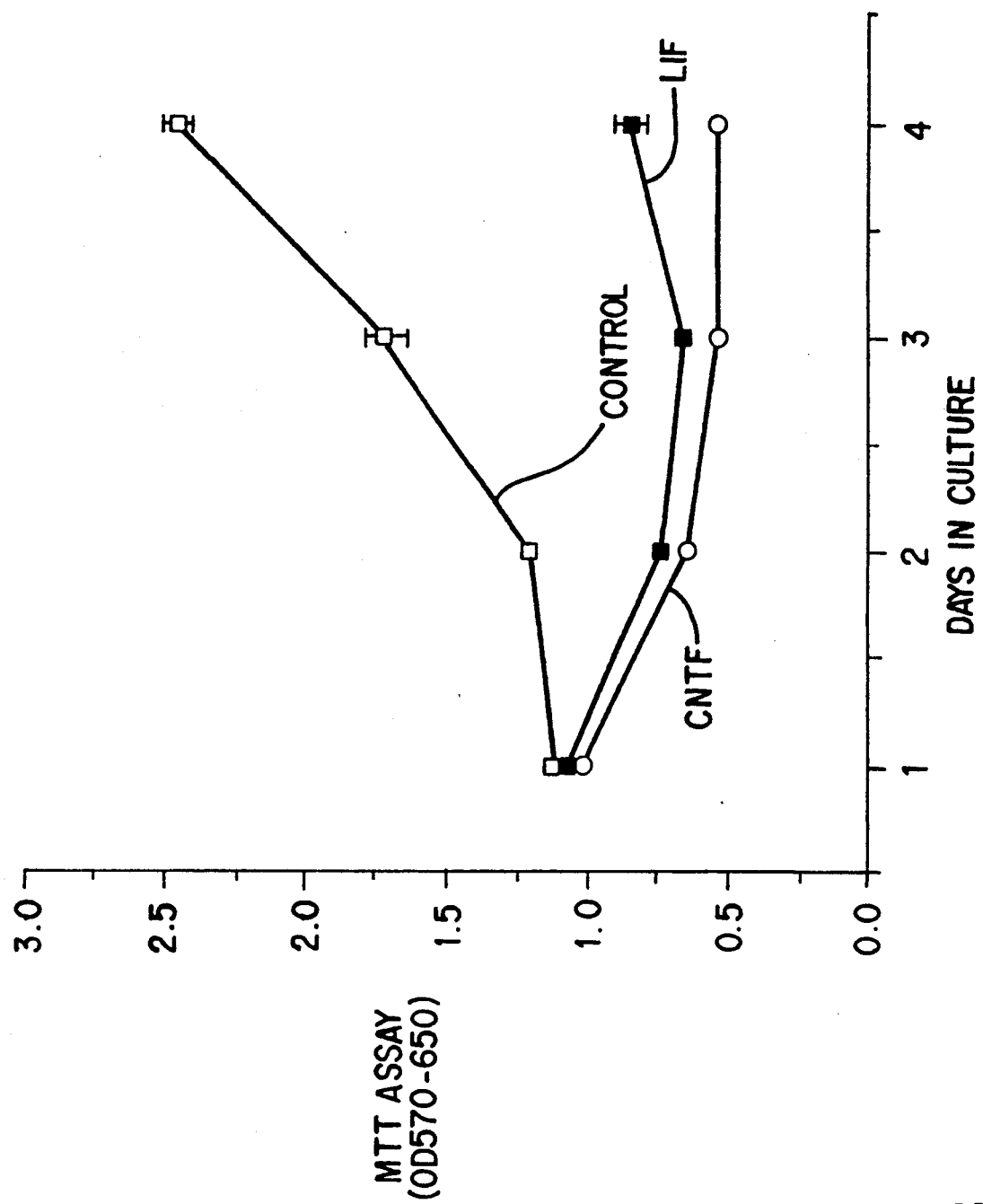

The MAH cell line utilized in this example was derived by immortalizing sympathoadrenal progenitors with the v-myc oncogene [Birren et al., Neuron 4:189-201 (1990)]. Treatment of MAH cells with CNTF dramatically blocked the increase in cell number that normally occurs upon the culture of these cells. LIF, which has effects on mature sympathetic neurons similar to those of CNTF, also blocked the normally occurring increase in MAH cell number of cells in CNTF- or LIF-treated cultures remained essentially constant over a 4 day period, while the control cultures continued to accumulate at an exponential rate (FIG. 7B). The effects of both CNTF and LIF displayed a very similar dose-dependency, with $EC_{50}$ values of approximately 50pg/ml (or 2 pM) (FIG. 7C); this dose-dependency is similar to that observed for the survival effect of CNTF on ciliary neurons [Masiakowski et al. J. Neurochem 57:1003-1012 (1991)]. Unlike either CNTF or LIF, basic fibroblast growth factor (FGF) acted as a potent mitogenic agent for these cells (FIG. 7C, inset), as shown previously [Birren et al., Neuron 4:189-201 (1990)].

Neither CNTF nor LIF induced neurite extension, or other morphological changes characteristic of neuronal differentiation, in MAH cells. However, cell cycle analysis showed that CNTF-treated MAH cells were arrested in the G1 phase of the cell cycle reminiscent of many factors that induce a transition between a proliferative state and cell differentiation. CNTF has been shown to induce cholinergic differentiation of sympathetic progenitors, and both CNTF and LIF induce cholinergic differentiation of mature sympathetic neurons. In order to pursue the possibility that CNTF and LIF may have a differentiative effect on MAH cells, we assayed for the induction of choline acetyltransferase (CHAT) activity in response to these ligands. As shown in FIG. 8A, treatment of MAH cells with CNTF or LIF resulted in an approximate 2-fold increase in ChAT activity while bFGF had no effect. Furthermore, exposure of MAH cells to CNTF for 24 hours led to an increase of low-affinity NGF receptor mRNA upon stimulation of PC12 cell differentiation by NGF.

Together, the above data suggests that CNTF acts as a growth arrest/differentiative factor for sympathoadrenal progenitor cells. These actions appear quite distinct from those of FGF. In addition to acting as a mitogenic agent for MAH cells, FGF induces neurite outgrowth and initiates neuronal differentiation (but not cholinergic differentiation) of these cells; FGF-induced differentiation may yield an NGF-dependent cell. Thus multiple factors may normally be capable of effecting the differentiation of neuronal progenitors. MAH cells appear to be a very useful model system in which to dissect the roles of various factors in mediating various aspects of neuronal differentiation.

9.2.2. CNTF and LIF Rapidly Induce Indistinguishable Patterns of Tyrosine Phosphorylation of Cellular Proteins Although cytokines do not utilize receptors which contain intrinsic tyrosine kinase activity, tyrosine phosphorylation is rapidly induced by a variety of different cytokines. To determine whether CNTF induces tyrosine phosphorylation in responsive cells, and to compare these phosphorylations with those induced by its distant structural relatives, we first examined CNTF and LIF responses in MAH cells as well as in neuroepitheliomas and Ewing's sarcoma. As shown in FIGS. 9A–9C, both CNTF and LIF rapidly induced tyrosine phosphorylation of three proteins (designated as $p200^{CLIP1}$, $p160^{CLIP2}$, and $p75^{CLIP3}$ for CNTF- and LIF-inducible phosphoproteins) in MAH cells, Ewing's sarcoma (EW-1), and neuroepithelioma (SK-N-LO). The induced phosphorylation patterns were indistinguishable for either factor in the different lines examined. Thus, CNTF-receptor positive cell lines with different phenotypic responses to CNTF (i.e., with respect to cell growth) displayed indistinguishable phosphorylation patterns in response to CNTF. The observed tyrosine phosphorylation responses were dose-dependent, with maximal induction obtained at 10 ng/ml for both CNTF and LIF.

To determine whether CLIP phosphorylations were specifically characteristic of CNTF and LIF responses, we compared CNTF and LIF phosphorylation patterns with those of FGF and NGF. Although both MAH and EW-1 cells are responsive to FGF, the CLIPs are not phosphorylated in response to FGF in either line (FIG. 9). Similarly, the CLIPs are not phosphorylated in response to NGF in the NGF-responsive pheochromocytoma cell line, PC12 (FIG. 10C).

A family of serine/threonine protein kinases designated as extracellular signal-regulated kinases, or ERKs, have recently been identified, characterized and molecularly cloned [Boulton et al., Cell 65:663–675 (1991)]. Activation of the ERKs, also known as MAP or MBP kinases, requires tyrosine phosphorylation [Boulton et al., Cell 65:663–675 (1991)] and rapidly occurs following the binding of receptor tyrosine kinases to their cognate ligands (e.g., for NGF, see FIG. 10C). The ERKs are also activated in response to a diverse set of both mitogenic and differentiative agents that do not utilize receptor tyrosine kinases. We chose to examine ERK phosphorylation in response to CNTF, LIF and FGF in EW-1 cells. In contrast to FGF, CNTF or LIF did not induce the rapid tyrosine phosphorylation of a 40 kD protein (FIG. 10A) that could be identified as ERK2 (FIG. 10B).

Our findings demonstrate that induction of $p200^{CLIP1}$, $p160^{CLIP2}$, and $p75^{CLIP3}$ tyrosine phosphorylation is characteristic of, and relatively specific for, the signal transduction pathways activated by CNTF and LIF. A protein similar in size to $p160CLIP^2$ is phosphorylated on tyrosine in response to both IL-6 and LIF [Nakajima and Wall, Mol. Cell. Biol. 11:1409–1418 (1991); Lord et El., Mol. Cell. Biol. 11:4371–4379 (1991)]; a possible relationship between these induced proteins will be addressed below. Unlike responses mediated by the CNTF and LIF receptors, responses which activate tyrosine kinase receptors, such as those induced by FGF and NGF, do not result in CLIP phosphorylation. Conversely, stimulation of tyrosine kinase receptors results in rapid activation of the ERKs, which are not rapidly phosphorylated by either CNTF or LIF.

9.2.3. The Rapid and Transient Phosphorylation of CLIPS Precedes Induction of a Characteristic Immediate Early Response Gene, TIS11

The induction of a signal transduction cascade initiated by ligand receptor interaction often proceeds with the activation of tyrosine phosphorylation and is then followed by the activation of immediate-early response genes. It has been previously reported that the activation of the immediate-early gene expression by both LIF and IL-6 is preceded by the rapid and transient tyrosine phosphorylation of p160 [Nakajima and Wall, Mol. Cell. Biol. 11:1409–1418 (1991); Lord et al., Mol. Cell. Biol. 11:4371–4379 (1991)]. In FIGS. 11A–11C, we have compared the time course of CNTF- and LIF-induced tyrosine phosphorylation of the CLIPs with the activation of immediate-early gene expression. We specifically examined the expression of one immediate early response gene, tis11, which appears to be characteristic of IL-6 mediated responses, as well as another immediate early response gene, c-fos, which does not appear to be specific for IL-6 responses. The induction of tyrosine phosphorylation of all three CLIPs by both CNTF and LIF in MAH cells was rapid, occurring within 5 minutes and were significantly decreased by 30 minutes (FIG. 11A). The phosphorylation kinetics for both factors were similar in EW-1 cells.

In MAH cells, CNTF and LIF both produced an induction in tis11 gene expression which followed the induction of CLIP phosphorylation. Maximal activation occurred at 45 minutes and returned to control levels by 120 minutes (FIG. 11B). Similar gene activation kinetics for tis11 were observed in EW-1 cells. No induction of c-los expression was observed in MAH cells with either CNTF or LIF (FIG. 11B). However, bFGF, unlike CNTF and LIF, induced c-fos gene expression in the absence of tis11 gene induction in MAH cells (FIG. 11C). CNTF and LIF induced both tis11 and c-fos (FIG. 11C) in EW-1 cells.

Our results suggest that rapid phosphorylation of the three CLIPS, followed by the induction of tis11 gene expression, characterizes both CNTF and LIF responses in neuronal cell lines.

Our results suggest that rapid phosphorylation of the three CLIPS, followed by the induction of tis11 gene expression, characterize both CNTF and LIF responses in neuronal cell lines. The timing of these events, together with the involvement of both a 160 kD phosphoprotein (CLIP2) as well as tis11, suggests similarities between the transduction pathway utilized by CNTF and LIF in neuronal cells and the pathway activated by IL-6 and LIF in hemopoietic cells. A direct comparison of the tyrosine phosphorylation events reveals striking similarities and differences. LIF induces the tyrosine phosphorylation of proteins identical in size to CLIP1, CLIP2 and CLIP3 in the M1 myeloid progenitor cell line, whereas IL-6 induces the tyrosine phosphorylation of only two of these proteins, corresponding to CLIP2 (presumably p160) and CLIP3; CNTF does not induce any detectable tyrosine phosphorylation in M1 cells (FIG. 12).

Specific phosphorylation events can be distinguished using different proteins kinase inhibitors. We utilized the protein kinase inhibitors staurosporine and H-7 to provide further evidence that CNTF- and LIF-induced phosphorylations are identical, and to determine whether the kinase cascades leading to tis11 activation are similar for CNTF, LIF and IL-6; H-7 was used because it specifically blocks a downstream kinase required for tis11 gene induction by IL-6 without affecting the initial tyrosine phosphorylation events [Nakajima and Wall, Mol. Cell. Biol. 11:1409–1418 (1991); Lord et al., Mol. Cell. Biol. 11:4371–4379 (1991)]. As shown in FIG. 13, both CNTF and LIF-induced tyrosine phosphorylation events were blocked by staurosporine, but not by H-7, in either MAH cells or EW-1 cells. However, H7 similarly blocked the induction of tis11 gene induction by CNTF and LIF in MAH cells (FIG. 13C) or by IL-6 and LIF in M1 cells (FIG. 13D); as expected from the phosphorylation data, staurosporine also blocked tis11 gene induction.

Thus a direct comparison of phosphorylation events, together with the use of protein kinase inhibitors, demonstrates that the signalling pathway activated by CNTF and LIF in neuronal cell lines corresponds to that utilized by LIF in hemopoietic cells. Furthermore, this pathway is distinguishable from, but shares many of the novel features of the IL-6 activated pathway in hemopoietic cells.

Thus the tis11 induction appears to be characteristic of responses to several of these distantly related cytokines, and the mechanism of induction by these different cytokines displays a similar sensitivity to protein kinase inhibitors.

The M1 cells did not express CNTF receptors and did not respond to CNTF, while the MAH, Ewing's sarcoma and neuroepithelioma cell lines examined did not respond to IL-6. The finding that cell lines can be found which segregate responsiveness to CNTF, LIF or IL-6 suggests that no two of these factors utilize an identical receptor.

9.2.4 Downregulation of CLIP1 and CLIP2 Due to Pretreatment with CNTF of LIF Cannot Be Reversed by CNTF or LIF Addition As would be expected if CNTF and LIF share signal transducing components, down-regulation of CLIP1 and CLIP2 phosphorylation due to pretreatment with CNTF or LIF could not be overcome by subsequent addition of the other factor (FIG. 14A). Furthermore, sub-saturating concentrations of these factors displayed additive effects for MAH cell growth inhibition while saturating concentrations were no longer additive.

9.2.5 Expression of CLIPS on the Cell Surface

To determine whether the CLIPs were expressed on the cell surface, we utilized an assay that specifically results in the biotinylation of cell surface proteins [Stahl et al., Biochemistry 29, 5405–5412 (1990)]. This assay revealed that CLIP1 and CLIP2 did indeed express extracellular domains that could be biotinylated (FIG. 14B); the surface location of CLIP1 was also consistent with the finding that its apparent size decreased upon peptide-N-glycosidase F treatment.

10. EXAMPLE: CHARACTERIZATION OF CLIP2

10.1 CLIP2 is Identical to gp130

The possibility that IL-6, CNTF and LIF share gp130 was investigated by using a monoclonal antibody (AM64) specific for human gp130 [Hibi et al., Cell 63:1149-1157 (1990)] in concert with a human cell line responsive to both CNTF and LIF. This antibody does not bind any gp130-related proteins, nor does it bind gp130 from rodent species. Immunoprecipitation of gp130 revealed that it was strongly tyrosine phosphorylated in response to either CNTF or LIF in EW-1 cells, and that this phosphorylated gp130 co-migrated with CLIP2 (compare lanes 3 and 7 with lanes 2 and 6 in FIG. 14C). Furthermore, the anti-gp130 antibody could be used to completely deplete CLIP2 from extracts of CNTF/LIF-induced EW-1 cells (compare lanes 4 and 8 with lanes 2 and 6 in FIG. 14C). From these data we infer that CLIP2 is indeed gp130, and thus that gp130 is tyrosine phosphorylated in response to both CNTF and LIF. Interestingly, CLIP1 partially co-precipitates with gp130 when using the AM64 antibody, suggesting that the two molecules may be found in a complex; less severe lysis conditions (e.g. using digitonin) were able to increase the amount of CLIP1 co-precipitating with gp130 in response to CNTF treatment.

10.2 ANTI-gp130 Antibody Selectively Blocked Tyrosine Phosphorylation of CLIPs and tis11 Induction EW-1 cells were starved for 1 hour in defined medium in the presence or absence of a cocktail of anti-gp130 antibodies (2ug/ml). The cells were treated for 5 minutes or 45 minutes with various factors prior to tyrosine phosphorylation assays and RNA analysis, respectively.

Anti-gp130 antibodies, which have been shown to inhibit IL-6 responses in hepatoma cell lines, were examined for their ability to block tyrosine phosphorylations induced by CNTF and LIF in EW-1 cells. The data demonstrates that tyrosine phosphorylations of CLIP1 and CLIP2(FIG. 17A) as well as tis11 gene expression (FIG. 17B), induced by CNTF or LIF were both completely blocked by anti-gp130 antibody. On the other hand, tyrosine phosphorylation induced by an unrelated ligand, EGF, was not affected.

10.3 gp130 is Expressed Ubiquitously whereas CNTFR Expression is More Limited It had previously been speculated that gp130 might function as a transducer for factors other than IL-6 based on the finding that gp130 transcripts were much more widely distributed than those for IL-6R [Hibi et al., Cell 63:1149–1157 (1990)]. Consistent with this notion and our finding that gp130 is shared by the CNTF and LIF signalling systems, we find that gp130 transcripts are expressed in both hemopoietic lines responsive to IL-6 (but not CN, TF) (FIG. 15, note M1 and B9 cell lines), as well as in adult brain tissue (FIG. 16) and neuronal lines responsive to CNTF and LIF (but not IL-6) (FIG. 15, note MAH, EW-1, SK-N-LO and SH-SYSY cell lines). In contrast, inCNTFR mRNA displays a restricted distribution and, in this experiment, is only expressed in the brain and in neuronal lines responsive to CNTF (FIG. 15).

EXAMPLE 11. RESPONSE OF ES CELLS TO CNTF

11.1 ES Cell Culture with LIF or CNTF

The 129/Sv//Ev XY ES cell line (gift from Elizabeth Robertson) used in this study was derived from a black, agouti (BB AA) mouse (Robertson et al. Nature 323, 445–448 (1986). Typically, ES cells were grown on a feeder layer of STO cells (growth-arrested with mitomycin C, Sigma Chemical Co.) and maintained in Dulbecco's modified Eagle media (DMEM, Irvine Scientific) supplemented with 10% FBS (Lot #11111020, Hyclone,), 0.1 mM $\beta$-mercaptoethanol (Sigma Chemical Co.), 292 mg/ml of L-glutamine, 100 U/ml penicillin G, and 100 mcg/ml streptomycin sulfate (100×stock of L-glutamine, penicillin and streptomycin sulfate, Irvine Scientific). As a precautionary step, LIF (recombinant human LIF, Amgen Biologicals) was added at a concentration of 10 ng/ml to prevent differentiation. ES cells were passaged every 3–4 days onto newly-made feeder cell plates as described previously ((Robertson et al. Nature 323, 445–448 (1986).

To determine the effect of CNTF on ES cells, STO cells and LIF were eliminated from the ES cell culture.

ES cells were passaged 2 times, in the presence of LIF (20 ng/ml), onto gelatin-coated plates (0.1% gelatin from porcine skin, Sigma Chemical Co.), few STO cells remained after the second passage. The ES cells were grown for 1 day in the presence of LIF (20 ng/ml), washed free of LIF, and then cultured in the presence of either CNTF, LIF or no factor for 7 days.

11.2 .RNA Analysis

Total RNA was prepared from ES cells, grown in the absence of STO feeder cells and maintained in the presence of LIF (20 ng/ml), by the guanidinium thiocyanate method as described (Chomczynski et al., Anal. Biochem. 162, 156-159 (1987). Ten micrograms of RNA was electrophoresed on a formaldehyde agarose gel, transferred to a nylon membrane (MSI), and hybridized to $^{32}$P labelled CNTF receptor cDNA probe (800 bp, Pst1 fragment) labelled by random oligo-priming (Stratagene).

11.3 CNTF Binding to ES Cells

Recombinant rat CNTF was iodinated using the Bolton-Hunter method (Bolton and Hunter, Biochem J. 133: 529-539. (1973). ES cells were plated at a density of $2.5 \times 10^6$ cells/35 mm well on gelatin plates and grown in the presence of 20 ng/ml LIF 4 days prior to binding. Media was removed from the wells and the cells were washed once with assay buffer (PBS, pH 7.4, containing BSA (1 mg/ml), 0.1 mM bacitracin, 1 mM PMSF and leupeptin (1 μg/ml)). The cells were incubated with $^{125}$I-rCNTF (700 pM) for 2 hrs at room temperature, followed by two quick washes with assay buffer. The cells were lysed with PBS containing 1% SDS and monitored for radioactivity.

11.4 Results

11.4.1 ES Cell Culture

ES cells maintained in the absence of feeder cells, but in the presence of LIF (10-20 ng/ml) remained as undifferentiated, compact colonies of small cells, However, lower concentrations of LIF (less than 10 ng/ml) resulted in the differentiation of the ES cells over a period of 2-7 days, as evidenced by the presence of endoderm-like cells and large, flat cells. Some cell death also occurred (FIG. 18, Panel A). To determine whether CNTF could also sustain ES cells in an undifferentiated state in the absence of feeder cells, ES cells were grown on gelatin plates with varying concentrations of CNTF. Low concentrations of CNTF, 5 pg/ml to 10 ng/ml CNTF, resulted in differentiation and some cell death. However, concentrations of greater than 10ng/ml up to 50 ng/ml CNTF maintained ES cells as small compact colonies of cells (FIG. 18, Panel B). ES cells maintained in the absence of either LIF or CNTF appeared endoderm-like or large and flat over a period of 2-7 days (FIG. 18, Panel C).

11.4.2 Expression of CNTFR in ES Cells

Northern analysis of RNA from ES cells indicated that CNTF receptor mRNA is present, albeit at low levels compared to adult rat brain (FIG. 19).

11.4.3 Binding of CNTF to ES Cells

ES cells exhibited 85% specific binding of $^{125}$I-rCNTF, with the total bound $cpm_{ave.} = 10235 + 157$ and the non-specific $cpm_{ave.} = 1517 + 163$.

11.4.4 Induction of tis11 by CNTF and LIF in ES Cells AND LIF IN ES CELLS

ES cells were plated onto gelatin-coated dishes and maintained in undifferentiated state in the presence of either CNTF (20 ng/ml) or LIF (20 ng/ml). The cells were washed twice in defined medium, starved for 2 hours in defined medium prior to the addition of CNTF (50ng/ml) or LIF (50ng/ml) for 45 minutes. Total cellular RNA was prepared, electrophoresed on a formaldehyde agarose gel, transferred to a nylon membrane (MSI), and hybridized to 32P-labelled tis11 probe (FIGS. 20A-20B). In ES cells, CNTF and LIF both produced similar inductions in tis11 gene expression, indicating responsiveness of ES cells to both of these cytokines.

REFERENCES

Various publications have been cited herein that are hereby incorporated by reference in their entirety.

---

What is claimed is:
1. A method of preventing the differentiation of ES cells comprising:
   a) obtaining ES cells
   b) culturing said ES cells in the presence of at least about 10 ng/ml ciliary neurotrophic factor.

* * * * *